(12) United States Patent
Iacono et al.

(10) Patent No.: US 11,491,473 B2
(45) Date of Patent: *Nov. 8, 2022

(54) SULFUR OXOACID-SUBSTITUTED AND PHOSPHORUS OXOACID-SUBSTITUTED POLYAROMATIC RESINS AND SALTS THEREOF AS PROMOTERS IN ACRYLATE PRODUCTION FROM COUPLING REACTIONS OF OLEFINS AND CARBON DIOXIDE

(71) Applicant: CHEVRON PHILLIPS CHEMICAL COMPANY LP, The Woodlands, TX (US)

(72) Inventors: Pasquale Iacono, Bartlesville, OK (US); Mark L. Hlavinka, Tulsa, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/169,951

(22) Filed: Feb. 8, 2021

(65) Prior Publication Data

US 2021/0178373 A1 Jun. 17, 2021

Related U.S. Application Data

(63) Continuation of application No. 16/598,199, filed on Oct. 10, 2019, now Pat. No. 10,926,247, which is a (Continued)

(51) Int. Cl.
*C07C 51/15* (2006.01)
*B01J 31/10* (2006.01)
(Continued)

(52) U.S. Cl.
CPC .......... *B01J 31/10* (2013.01); *B01J 31/0255* (2013.01); *B01J 31/08* (2013.01); *B01J 31/2295* (2013.01);
(Continued)

(58) Field of Classification Search
CPC ........ B01J 31/08; B01J 31/10; B01J 31/0255; B01J 31/2295; B01J 2231/321; C07C 51/04; C07C 51/15
See application file for complete search history.

(56) References Cited

U.S. PATENT DOCUMENTS 3,623,973 A 11/1971 Tarhan
4,060,480 A 11/1977 Reed et al.
(Continued)

FOREIGN PATENT DOCUMENTS

CA 2791834 A1 9/2011
CN 103785469 A 5/2014
(Continued)

OTHER PUBLICATIONS

Al-Ghamdi, et al., "Activity Relationship To Screen Ni-Bisphosphine Complexes for the Oxidative Coupling of CO2 and Ethylene," Organometallics, 2017, vol. 36, pp. 1107-1112.
(Continued)

*Primary Examiner* — Yate'K Cutliff
(74) *Attorney, Agent, or Firm* — Evershaeds Sutherland (US) LLP

(57) ABSTRACT

This disclosure provides for catalyst systems and processes for forming an α,β-unsaturated carboxylic acid or a salt thereof. In an aspect, the catalyst system can comprise: a transition metal precursor comprising a Group 8-11 transition metal and at least one first ligand; optionally, at least one second ligand; an olefin; carbon dioxide (CO$_2$); a diluent; and an oxoacid anion-substituted polyaromatic resin com-
(Continued)

prising a sulfonated polyaromatic resin, a phosphonated polyaromatic resin, a sulfinated polyaromatic resin, a thiosulfonated, or a thiosulfinated polyaromatic resin, and further comprising associated metal cations. Methods of regenerating the polyaromatic resin with associated metal cations are described.

34 Claims, 1 Drawing Sheet

Related U.S. Application Data continuation of application No. 16/001,174, filed on Jun. 6, 2018, now Pat. No. 10,550,061.

(60) Provisional application No. 62/519,556, filed on Jun. 14, 2017.

(51) Int. Cl.
    *B01J 31/02*     (2006.01)
    *C07C 51/09*     (2006.01)
    *B01J 31/08*     (2006.01)
    *B01J 31/22*     (2006.01)

(52) U.S. Cl.
    CPC .............. *C07C 51/09* (2013.01); *C07C 51/15* (2013.01); *B01J 2231/321* (2013.01)

(56) References Cited

U.S. PATENT DOCUMENTS

| | | | |
|---|---|---|---|
| 4,452,910 A | 6/1984 | Hopkins et al. | |
| 4,792,620 A | 12/1988 | Paulik et al. | |
| 5,376,611 A | 12/1994 | Shveima | |
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 7,250,510 B2 | 7/2007 | Organ et al. | |
| 7,294,599 B2 | 11/2007 | Jensen et al. | |
| 7,601,665 B2 | 10/2009 | McDaniel et al. | |
| 7,884,163 B2 | 2/2011 | McDaniel et al. | |
| 8,309,485 B2 | 11/2012 | Yang et al. | |
| 8,592,632 B2 | 11/2013 | Dahmen et al. | |
| 8,623,973 B1 | 1/2014 | McDaniel et al. | |
| 8,642,803 B2 | 2/2014 | Limbach et al. | |
| 8,697,909 B2 | 4/2014 | Limbach et al. | |
| 8,703,886 B1 | 4/2014 | Yang et al. | |
| 8,940,940 B2 | 1/2015 | Dehn et al. | |
| 9,023,959 B2 | 5/2015 | McDaniel et al. | |
| 9,416,087 B2 | 8/2016 | Hlavinka et al. | |
| 2010/0076167 A1 | 3/2010 | McDaniel et al. | |
| 2011/0218359 A1 | 9/2011 | Limbach et al. | |
| 2013/0172616 A1 | 7/2013 | Limbach et al. | |
| 2015/0343431 A1 | 12/2015 | Parvulescu et al. | |
| 2015/0344394 A1 | 12/2015 | Parvulescu et al. | |
| 2016/0102039 A1 | 4/2016 | Hlavinka et al. | |
| 2016/0130208 A1 | 5/2016 | Schaffner et al. | |
| 2016/0229782 A1 | 8/2016 | Hlavinka et al. | |
| 2016/0311745 A1 | 10/2016 | Hlavinka et al. | |
| 2017/0166506 A1 | 6/2017 | Iacono et al. | |

FOREIGN PATENT DOCUMENTS

| | | | |
|---|---|---|---|
| CN | 104418719 A | 3/2015 | |
| CN | 104418736 A | 3/2015 | |
| CN | 104418737 A | 3/2015 | |
| CN | 105622383 A | 6/2016 | |
| CN | 105622400 A | 6/2016 | |
| DE | 112014001125 A5 | 11/2015 | |
| IN | 201207472 P4 | 12/2013 | |
| IN | 201404656 P4 | 9/2015 | |
| WO | 2011/107559 A2 | 9/2011 | |
| WO | 2011/107559 A3 | 12/2011 | |
| WO | 2013/098772 A1 | 7/2013 | |
| WO | 2013/186238 A1 | 12/2013 | |
| WO | 2014/003195 A1 | 1/2014 | |
| WO | 2014/130410 A1 | 8/2014 | |
| WO | 2014/198469 A1 | 12/2014 | |
| WO | 2015/018793 A1 | 2/2015 | |
| WO | 2015/132031 A1 | 9/2015 | |
| WO | 2015/173276 A1 | 11/2015 | |
| WO | 2015/173277 A1 | 11/2015 | |
| WO | 2015/173295 A1 | 11/2015 | |
| WO | 2015/173296 A1 | 11/2015 | |
| WO | 2015/173307 A1 | 11/2015 | |
| WO | 2015/197699 A1 | 12/2015 | |
| WO | 2016/057449 A1 | 4/2016 | |
| WO | 2017/178282 A1 | 10/2017 | |

OTHER PUBLICATIONS

Brand, et al., "Acid-Base Characterization of Aluminum Oxide Surfaces with XPS" J. Phys. Chem. B. 2004, 108, p. 6017-6024.
Bruckmeier, et al., "Formation of Methyl Acrylate from CO2 and Ethylene via Methylation of Nickelalactones", Organometallics, 2010, vol. 29, pp. 2199-2202.
Deutschmann, "Heterogeneous Catalysis and Solid Catalysts, 2. Development and Types of Solid Catalysts," Ullmann's Encyclopedia of Industrial Chemistry, published online Oct. 15, 2011, pp. 483-549, doi: 10.1002/14356007.o05_o02.
Eigenberger, "Catalytic Fixed-Bed Reactors," Ullmann's Encyclopedia of Industrial Chemistry, 2012, pp. 1-66, doi:10.1002/14356007.b04_199.pub2.
Final Office Action for U.S. Appl. No. 15/091,794, dated Feb. 7, 2017.
Fischer, et al., "A key step in the formation of acrylic acid from CO2 and ethylene: the transformation of a Nickelalactone into a nickel-acrylate complex"; Chem. Commun., 2006, pp. 2510-2512.
Fischer, et al., "Zur Synthese und Charakterisierung van N, N'—Tetramethylethylendiamin-nickelacyclopropionat", Z. anorg. allg. Chem., 1989, vol. 577, pp. 111-114.
Gordillo, et al., "Catalytic route to acrylates from alkenes and CO2" Abstracts of Papers, 245th ACS National Meeting & Exposition, New Orleans, LA, United States, Apr. 7-11, 2013 (2013), INOR-1109. Language: English, Database: CAPLUS.
Hendricksen, "Catalytic Formation of Acrylate from Carbon Dioxide and Ethene," Chemistry, A European Journal, 2014, vol. 20, pp. 12037-12040.
Hoberg, et al., "Nickel(O)-Induzierte C-C-Verknüpfung Zwischen Kohlendioxid und Ethylen Sowie Mono-Oder Di-Substituierten Alkenen"; Journal of Organometallic Chemistry, 1983, vol. 251, pp. C51-C53.
Huguet, et al., "Nickel-Catalyzed Direct Carboxylation of Olefins with CO2: One-Pot Synthesis of a, β-Unsaturated Carboxylic Acid Salts", Chem. Eur. J., 2014, vol. 20, pp. 16858-16862.
International Search Report and the Written Opinion of the International Searching Authority in PCT/US2017/025837 dated Jul. 17, 2017, 9 pages.
International Search Report and Written Opinion for PCT/US2016/066360, dated Jul. 27, 2017, 8 pages.

(56) References Cited

OTHER PUBLICATIONS

International Search Report and Written Opinion of the Kal Searching Authority, PCT/US2015/054128, dated Dec. 21, 2015, 11 pages.
Jin, et al., "Effect of Sodium Cation on Metallacycle β-Hydride Elimination in CO2-Ethylene Coupling to Acrylates", Chem. Eur. J., 2014, vol. 20, pp. 1-8.
Jin, et al., "Lewis Acid Induced β-Elimination from a Nickelalactone: Efforts toward Acrylate Production from CO2 and Ethylene", Organometallics, 2013, vol. 32, pp. 2152-2159.
Knopf, et al., "A family of cis-macrocyclic diphosphines: modular, stereoselective synthesis and application in Catalytic CO2/ethylene coupling", Chemical Science, 2017, vol. 8 (Issue 2), pp. 1463-1468. doi:10.1039/c6sc03614g.
Kraus, et al., "Ni-Catalyzed Synthesis of Acrylic Acid Derivatives from CO2 and Ethylene," Topics in Organometallic Chemistry, vol. 53, 2015, p. 199-223.
Langer, et al., "A new set of nickelacyclic carboxylates ("nickelalactones") containing pyridine as supporting ligand: synthesis, structures and application in C—C- and C—S linkage reactions"; Journal of Organometallic Chemistry, 2004, vol. 689, pp. 2952-2962.
Krillov, et al., "Carboxylic acid derivatives via catalytic carboxylation of unsaturated hydrocarbons: whether the nature of a reductant may determine the mechanism of CO2 incorporation?", Dalton Trans., 2015, vol. 44, 16212-16223.
Lejkowski, et al., "The First Catalytic Synthesis of an Acrylate from CO2 and an Alkene—A Rational Approach"; Chem. Eur. J., 2012, vol. 18, pp. 14017-14025.
Limbach, "Acrylates from Alkenes and CO2, the Stuff That Dreams Are Made of," Advances in Organometallic Chemistry 2015, vol. 63, Chapter 4, pp. 175-202.
Limbach, et al., "CO2 as C1 building block for the synthesis of acrylates and beyond", From Abstracts of Papers, 247th ACS National Meeting & Exposition, Dallas, TX, United States, Mar. 16-20, 2014 (2014), CATL-116. Language: English, Database: CAPLUS.
Limbach, et al., "Investigation of fundamental steps in the formation of acrylates from CO2 and ethylene", Abstracts of Papers, 243rd ACS National Meeting & Exposition, San Diego, CA, United States, Mar. 25-29, 2012 (2012), NOR-1216. Language: English, Database: CAPLUS.
Manzini, et al., "Enhanced activity and recyclability of palladium complexes in the catalytic synthesis of sodium acrylate from CO2 and ethylene" ChemCatChem, 2016. doi:10.1002/cctc.201601150.
Manzini, et al., "Palladium- and Nickel-Catalyzed Synthesis of Sodium Acrylate from Ethylene, CO2, and Phenolate Bases: Optimization of the Catalytic System for a Potential Process", Eur. J. Org. Chem., 2015, pp. 7122-7130.
Manzini, et al., "Synthesis of acrylates from olefins and CO2 using sodium alkoxides as bases", Catalysis Today, 2016, http://dx.doi.org/10.1016/j.cattod.2016.03.025.
Newkirk, "Drying and Decomposition of Sodium Carbonate," Analytical Chemistry, vol. 30, No. 5, 1958, pp. 982-984.
Non-Final Office Action for U.S. Appl. No. 15/203,844, dated Jan. 12, 2017.
Non-Final Office Action for U.S. Appl. No. 14/509,082 dated Nov. 5, 2015.
Norskov, et al., Nature Chemistry, Towards the Computational Design of Solid Catalysts, 2009, 1, pp. 37-46.
Papai, et al., "Mechanistic Details of Nickel(O)-Assisted Oxidative Coupling of CO2 with C2H4"; Organometallics, vol. 23, pp. 5252-5259, 2004.
Pinnavaia, T. J., "Intercalated Clay Catalysts," Science, 1983, vol. 220, No. 4595, pp. 365-371.
Plessow, et al., "Acrylate Formation from CO2 and Ethylene Mediated by Nickel Complexes: A Theoretical Study", Oganometallics, 2014, vol. 33, pp. 3657-3668.
Plessow, et al., "Mechanistic Details of the Nickel-Mediated Formation of Acrylates from CO2, Ethylene and Methyllodide", Organometallics, 2013, vol. 32, pp. 3327-3338.
Prasetyo, "Development of heterogenized catalyst systems for the synthesis of acrylic acid derivatives from carbon dioxide and ethylene," University of Stuttgart, Doctoral Thesis, Date of oral test: Apr. 20, 2015, 275 pages.
Stieber, et al., "Acrylate formation from CO2 and ethylene: catalysis with palladium and mechanistic insight", Chem. Commun., 2015, vol. 51, pp. 10907-10909.
Thomas, J.M., "Sheet Silicate Intercalates: New Agents for Unusual Chemical Conversions*", Intercalation Chemistry, Academic Press, Inc., 1982, Ch. 3, pp. 55-99.
Wang, et al., "Synthesis of Acrylic Acid Derivatives from CO2 and Ethylene," Chem, 3, 211-228, 2017.
Yu, et al., "Carboxylation of olefins/alkynes with CO2 to industrially relevant acrylic acid derivatives", Journal of CO2 Utilization, 2013, vol. 1, pp. 60-68.
Gelbard, Georges. Organic Synthesis by Catalysis with Ion-Exchange Resins. Ind. Eng. Chem. Res. vol. 44, No. 23. Oct. 14, 2005. pp. 8468-8498.

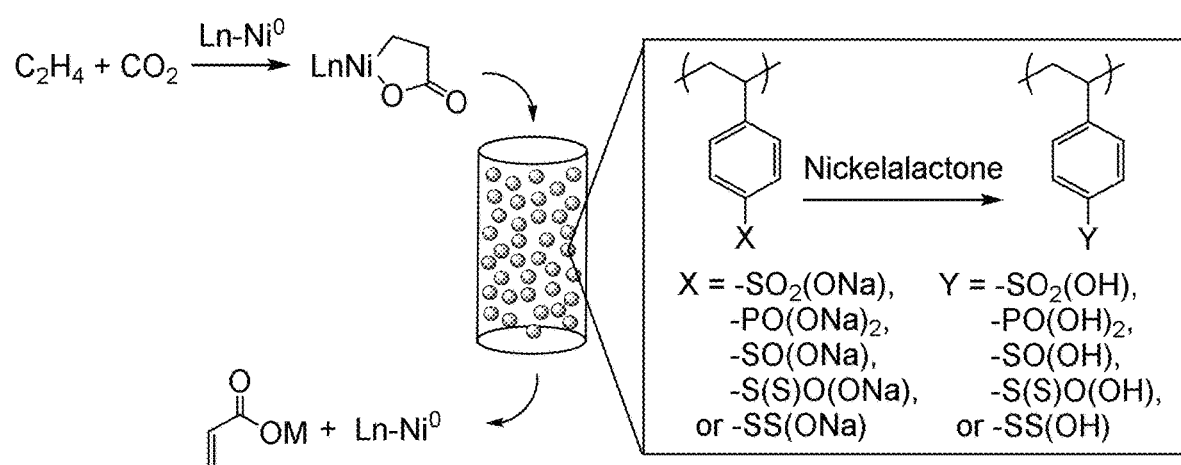

SULFUR OXOACID-SUBSTITUTED AND PHOSPHORUS OXOACID-SUBSTITUTED POLYAROMATIC RESINS AND SALTS THEREOF AS PROMOTERS IN ACRYLATE PRODUCTION FROM COUPLING REACTIONS OF OLEFINS AND CARBON DIOXIDE

CROSS REFERENCE TO RELATED APPLICATIONS

This application is a continuation of U.S. patent application Ser. No. 16/598,199, filed Oct. 10, 2019, now U.S. Pat. No. 10,926,247, which is a continuation of U.S. patent application Ser. No. 16/001,174, filed Jun. 6, 2018, now U.S. Pat. No. 10,550,061, which claims the benefit of priority of U.S. Provisional Patent Application No. 62/519,556, filed Jun. 14, 2017, each of which is incorporated herein by reference in its entirety.

TECHNICAL FIELD

This disclosure relates to routes of synthesis of acrylic acid, other α,β-unsaturated carboxylic acids and salts thereof, including catalytic methods.

BACKGROUND

The majority of industrially synthesized chemical compounds are prepared from a limited set of precursors, whose ultimate sources are primarily fossil fuels. As these reserves diminish, it would be beneficial to use a renewable resource, such as carbon dioxide, which is a non-toxic, abundant, and economical $C_1$ synthetic unit. The coupling of carbon dioxide with other unsaturated molecules holds tremendous promise for the direct preparation of molecules currently prepared by traditional methods not involving $CO_2$.

One could envision the direct preparation of acrylates and carboxylic acids through this method, when carbon dioxide is coupled with olefins. Currently, acrylic acid is produced by a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced.

Therefore, what is needed are improved methods for preparing acrylic acid and other α,β-unsaturated carboxylic acids, including catalytic methods.

SUMMARY OF THE DISCLOSURE

This summary is provided to introduce various concepts in a simplified form that are further described below in the detailed description. This summary is not intended to identify required or essential features of the claimed subject matter nor is the summary intended to limit the scope of the claimed subject matter.

In an aspect, this disclosure provides processes, including catalytic processes, for producing α,β-unsaturated carboxylic acids or salts thereof utilizing a soluble or an insoluble form of a sulfonated polyaromatic resin system or a phosphonated polyaromatic resin system. When the sulfonated or the phosphonated polyaromatic resin system is insoluble or the reaction system is otherwise heterogeneous, these processes represent an improvement over homogeneous processes that result in poor yields and involve challenging separation and/or isolation procedures. Therefore, conventional methods generally make isolation of the desired α,β-unsaturated carboxylic acid (e.g., acrylic acid) difficult. In contrast, the processes disclosed herein utilize a sulfur oxoacid anion-substituted polyaromatic resin or a phosphorus oxoacid anion-substituted polyaromatic resin; wherein the polyaromatic resin further comprises associated metal cations that generally provides a heterogeneous reaction mixture. When combined with a catalyst such as a nickel catalyst, ethylene and carbon dioxide can be coupled to form a metalalactone, and the sulfonated or the phosphonated polyaromatic resin can subsequently destabilize the metalalactone which eliminates a metal acrylate. By developing the disclosed heterogeneous system, there is now provided a distinct advantage in ease of separation of the desired product from the catalytic system. Moreover, the sulfonated or the phosphonated polyaromatic resin s can result in surprisingly high yields of the desired α,β-unsaturated carboxylic acid, such as acrylic acid.

According to an aspect, this disclosure provides a process for forming an α,β-unsaturated carboxylic acid or salt thereof, the process comprising:
  a) contacting
    1) a metalalactone compound;
    2) a diluent; and
    3) a sulfur oxoacid anion-substituted polyaromatic resin or a phosphorus oxoacid anion-substituted polyaromatic resin; wherein the polyaromatic resin further comprises associated metal cations to provide a reaction mixture; and
  b) applying reaction conditions to the reaction mixture suitable to form the α,β-unsaturated carboxylic acid or the salt thereof.

According to this and other aspects of the disclosure, the metalalactone compound may also be described as a metalalactone comprising at least one ligand or simply a metalalactone, and these terms are used interchangeably to reflect that the metalalactone compound comprises at least one ligand in addition to the metalalactone moiety. Similarly, reference to a metalalactone ligand refers to any ligand of the metalalactone compound other than the metalalactone moiety.

In another aspect, there is provided a process for forming an α,β-unsaturated carboxylic acid or a salt thereof, the process comprising:
  a) contacting
    1) a metalalactone compound;
    2) a diluent; and
    3) a sulfur oxoacid anion-substituted polyaromatic resin or a phosphorus oxoacid anion-substituted polyaromatic resin; wherein the polyaromatic resin further comprises associated metal cations, to provide a reaction mixture comprising an adduct of the metalalactone compound and sulfur oxoacid anion-substituted polyaromatic resin or a phosphorus oxoacid anion-substituted polyaromatic resin; and
  b) applying reaction conditions to the reaction mixture suitable to induce a metalalactone elimination reaction to produce the α,β-unsaturated carboxylic acid or the salt thereof.

Still another aspect of this disclosure provides a process for producing an α,β-unsaturated carboxylic acid or a salt thereof, the process comprising:
  a) contacting in any order
    1) a transition metal precursor compound comprising at least one first ligand;

2) optionally, at least one second ligand;
3) an olefin;
4) carbon dioxide ($CO_2$);
5) a diluent; and
6) a sulfur oxoacid anion-substituted polyaromatic resin or a phosphorus oxoacid anion-substituted polyaromatic resin; wherein the polyaromatic resin further comprises associated metal cations to provide a reaction mixture; and b) applying reaction conditions to the reaction mixture suitable to form the α,β-unsaturated carboxylic acid or the salt thereof.

This summary and the following detailed description provide examples and are explanatory only of the invention. Accordingly, the foregoing summary and the following detailed description should not be considered to be restrictive. Additional features or variations thereof can be provided in addition to those set forth herein, such as for example, various feature combinations and sub-combinations of these described in the detailed description.

BRIEF DESCRIPTION OF THE DRAWINGS

The FIG. illustrates an embodiment or aspect of this disclosure, showing the use a sulfur oxoacid anion-substituted polyaromatic resin or a phosphorus oxoacid anion-substituted polyaromatic resin stationary phase in a column configuration, in which formation of the acrylate coupling reaction of ethylene and $CO_2$ to form a metalalactone such as a nickelalactone in a mobile phase can be effected, and the resulting nickelalactone destabilized by the polyelectrolyte stationary phase to form an acrylate product.

DETAILED DESCRIPTION OF THE DISCLOSURE

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "a sulfonated polyaromatic resin," "a diluent," "a catalyst," and the like, is meant to encompass one, or mixtures or combinations of more than one sulfonated polyaromatic resin, diluent, catalyst, and the like, unless otherwise specified.

The terms "including", "with", and "having", as used herein, are defined as comprising (i.e., open language), unless specified otherwise.

The term "hydrocarbon" refers to a compound containing only carbon and hydrogen. Other identifiers can be utilized to indicate the presence of particular groups in the hydrocarbon, for instance, a halogenated hydrocarbon indicates the presence of one or more halogen atoms replacing an equivalent number of hydrogen atoms in the hydrocarbon.

As used herein, the term "α,β-unsaturated carboxylic acid" and its derivatives refer to a carboxylic acid having a carbon atom of a carbon-carbon double bond attached to the carbonyl carbon atom (the carbon atom bearing the double bonded oxygen atom). Optionally, the α,β-unsaturated carboxylic acid can contain other functional groups, heteroatoms, or combinations thereof.

The term "polyelectrolyte" is used herein to mean a polymeric (macromolecular) substance which comprises a multiply-charged polyanion, polycation, or a copolymer thereof comprising of either a statistical or predetermined distribution and/or sequencing of the individual monomer units (e.g. block versus random copolymer). These polyions are generally stabilized by a stoichiometric amount of counter ions inherently present in the polymeric substance. Therefore, an "anionic polyelectrolyte" refers to a polyelectrolyte that comprises a multiply-charged polyanion, together with an equivalent amount of cations. The charge on the polyion typically resides on heteroatoms such as oxygen, nitrogen, or sulfur, or on groups such as sulfonate or phosphonate. The structural part of the polyelectrolyte that bears the charged moieties can be pendant groups off a polymer backbone or can be part of the polymeric backbone itself. The term "polyelectrolyte" is used to refer to both soluble species and insoluble species, such as some of the functionalized poly(vinylbenzene)-based materials and the phenol-formaldehyde type resins described herein. For example, the sulfur oxoacid anion-substituted and the phosphorus oxoacid anion-substituted polystyrene type resins further comprise associated metal cations are referred to as "polyelectrolytes". The multiply-charged polyanion of such polyelectrolytes may also be referred to as a base, and the associated metal ions as simply a counter ion, metal ion, or Lewis acid as appropriate. As used herein, terms "polyelectrolyte" and "anionic polyelectrolyte" are used interchangeably with terms such as polyaromatic, polyaromatic polymer, polyaromatic resin, solid activator, and co-catalyst, and all these terms are used to refer to either the acid form of the polymer or its corresponding anionic polymer (salt form), as the context requires or allows.

The term "polyaromatic" or "polyaromatic resin" is used herein to describe a neutral, acid form polymer or its corresponding anionic, salt form polymer derived therefrom, in which the aromatic moiety is substituted with an acid-functional group that can be deprotonated to form an anionic polyelectrolyte comprising associated metal ions. Specifically, the polyaromatic resin of this disclosure is a sulfur oxoacid-substituted substituted polyaromatic resin or a phosphorus oxoacid-substituted polyaromatic resin, or salts thereof. Therefore, the terms "polyaromatic" or "polyaromatic resin" refer to the functionalized forms. For example, the neutral, acid form polyaromatic resins of this disclosure include the sulfonic acid-substituted or the phosphonic acid-substituted polystyrene (poly(vinylbenzene)) polymers and copolymers, or any suitable sulfonic acid-substituted or the phosphonic acid-substituted polymer. The anionic salt form polyaromatic resins of this disclosure include, for example, the sulfonated, the phosphonated, the sulfinated, the thiosulfonated and/or the thiosulfinated polystyrene polymers and copolymers, or any suitable sulfonated, phosphonated, sulfinated, thiosulfonated, or thiosulfinated polymer. Moreover, terms such as polyaromatic or polyaromatic resin are generally used herein to describe specific types of polymers that are somewhat different from each other, as set out here.

[1] In one aspect, the term polyaromatic or polyaromatic resin are used to describe a type of polymer that typically includes a pendant aromatic group bonded to a polymeric backbone, in which the pendant aromatic group is acid-functionalized or one in which the acid-functional substituent on the pendant aromatic group has been converted to its salt form. Substituted analogs of these acid form and salt form polymers are encompassed in this group. For example, these terms describe the neutral sulfonic acid-substituted or the neutral phosphonic acid-substituted polystyrene polymers and copolymers (such as copolymers with divinylbenzenes), and also used to describe the sulfonated or the phosphonated polystyrene polymers and copolymers, as the context requires or allows. Pyrolyzed variants of these polymers, which comprise porous carbonaceous materials are also included in this disclosure.

[2] According to another aspect, the term polyaromatic or polyaromatic resin are also generally used herein to describe, for example, an aromatic resin such as an extended crosslinked network derived from phenolic (phenol-formaldehyde) resins, and comprising aromatic moieties that have been functionalized with sulfonic acid groups, phosphonic acid groups, sulfinic acid groups, thiosulfonic acid groups and/or thiosulfinic acid groups. Generally, these resins are accessible from either reacting phenol compounds that are sulfur oxoacid acid or anion-functionalized and/or phosphorus acid or oxoacid anion-functionalized (e.g. sulfonated, phosphonated, sulfinated, thio sulfonated, and/or thiosulfinated) with formaldehyde under polymerization conditions to form functionalized phenolic resins. Alternatively, these resins are also accessible by generating the phenolic (phenol-formaldehyde) resins in a conventional fashion and functionalizing these phenolic type resins with sulfonic acid groups, phosphonic acid groups, sulfinic acid groups, thiosulfonic acid groups, and/or thiosulfinic acid groups. Pyrolyzed variants of these phenolic type resins, which comprise porous carbonaceous materials are also included in this disclosure.

Examples of this type of polyaromatic resin include, but are not limited to, sulfonated polyaromatic resins that can be generated by sulfuric acid treatment of a crosslinked polystyrene or a porous carbonaceous material derived from the pyrolysis of a phenol formaldehyde resin. Other examples of this type of polyaromatic resin include, but are not limited to, sulfur oxoacid anion-substituted polyaromatic resins generated by $SO_2$ treatment (e.g. $SO_2$(aq)), sulfonic acid treatment, sulfinic acid treatment, thiosulfonic acid treatment, or thiosulfinic acid treatment of a crosslinked polystyrene or a porous carbonaceous material derived from the pyrolysis of a phenol formaldehyde resin. Examples of this type of polyaromatic resin also include phosphonated polyaromatic resins that can be generated by phosphonic acid treatment of a crosslinked polystyrene or a porous carbonaceous material derived from the pyrolysis of a phenol formaldehyde resin. Phosphonated polyaromatic resins also may be generated by aromatic substitution with a chlorinated phosphine of a crosslinked polystyrene or a porous carbonaceous material derived from the pyrolysis of a phenol formaldehyde resin, followed by for example, an alcoholic or aqueous workup. The underlying phenol-formaldehyde crosslinked resins and their substituted analogs that can be used in preparing the sulfur oxoacid anion-substituted polyaromatic resin or the phosphorus oxoacid anion-substituted polyaromatic resin include the phenol aromatic group and methylene moieties as part of an extended crosslinked network. The skilled person will understand that pyrolysis of these materials can generate porous carbonaceous materials that can be functionalized as described.

A "polyhydroxyarene" is used herein to a phenol-type monomer that includes more than one hydroxyl group. Resorcinol (also termed, benzenediol or m-dihydroxybenzene) is a typical polyhydroxyarene. Polyhydroxyarenes are used in the formation of Bakelite™ type resins with formaldehyde, that can be further functionalized with a sulfur oxoacid or a phosphorus oxoacid, or a salt form thereof, such as a sulfonate, phosphonate, sulfinated, thiosulfonated, or thiosulfinated groups.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Various numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicants disclose in an aspect of the disclosure that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means ±20% of the stated value, ±15% of the stated value, ±10% of the stated value, ±5% of the stated value, or ±3% of the stated value.

Applicants reserve the right to proviso out or exclude any individual members of any such group of values or ranges, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants can be unaware of at the time of the filing of the application.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group can also be referred to herein as "unsubstituted" or by equivalent terms such as "non-substituted," which refers to the original group or compound. "Substituted" is intended to be non-limiting and include inorganic substituents or organic substituents as specified and as understood by one of ordinary skill in the art.

The terms "contact product," "contacting," and the like, are used herein to describe compositions and methods wherein the components are contacted together in any order, in any manner, and for any length of time, unless specified otherwise. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

The Abstract of this application is not intended to be used to construe the scope of the claims or to limit the scope of the subject matter that is disclosed herein, but rather to satisfy the requirements of 37 C.F.R. § 1.72(b), to enable the United States Patent and Trademark Office and the public generally to determine quickly from a cursory inspection the nature and gist of the technical disclosure. Moreover, any headings that are employed herein are also not intended to be used to construe the scope of the claims or to limit the scope of the subject matter that is disclosed herein. Any use of the past tense to describe any example otherwise indicated as constructive or prophetic is not intended to reflect that the constructive or prophetic example has actually been carried out.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

The present disclosure is directed generally to methods for forming α,β-unsaturated carboxylic acids, or salts thereof. An illustrative example of a suitable α,β-unsaturated carboxylic acid is acrylic acid.

According to one aspect, this disclosure provides for the formation of an α,β-unsaturated carboxylic acids and salts thereof from metalalactones and polyaromatics such as those functionalized polyaromatic resins described here. One example of the α,β-unsaturated carboxylic acid salt formation from exemplary metalalactones and a sulfur oxoacid anion-substituted polyaromatic resin or a phosphorus oxoacid anion-substituted polyaromatic resin is illustrated in Scheme 1, which provides for a nickel catalytic coupling reaction between an olefin and $CO_2$ and formation of an acrylate. As explained herein, Scheme 1 is not limiting but is exemplary, and each reactant, catalyst, polymer, and product are provided for illustrative purposes.

Scheme 1

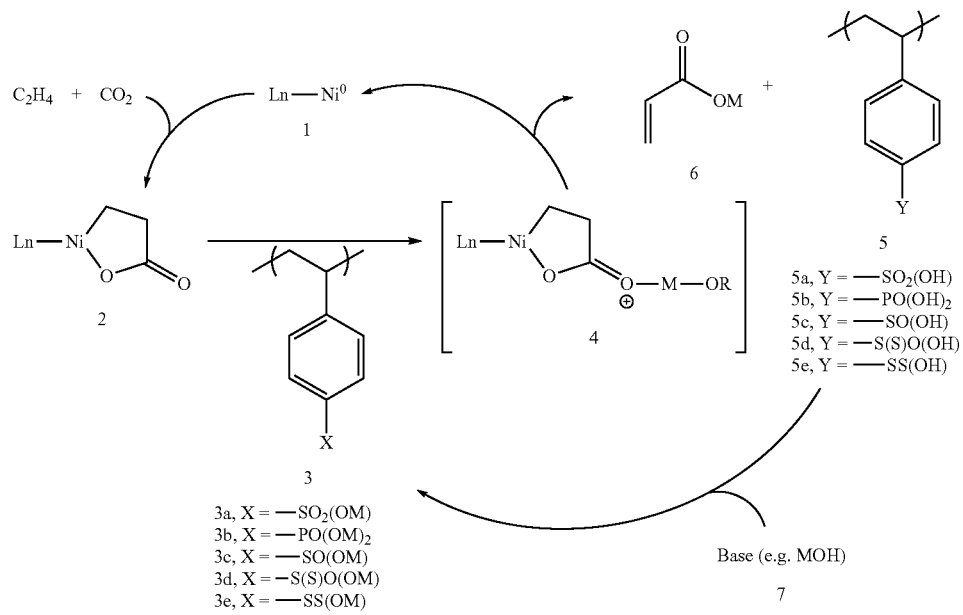

In Scheme 1, a transition metal catalyst as disclosed herein is illustrated generally by a nickel(0) catalyst at compound 1, and the olefin disclosed herein, generally an α-olefin, is illustrated generally by ethylene. In the presence of the catalyst 1, the olefin couples with $CO_2$ to form the metalalactone 2. Metalalactone 2 is destabilized by its interaction with a sulfur oxoacid anion-substituted polyaromatic resin or a phosphorus oxoacid anion-substituted polyaromatic resin 3, examples of which is shown in Scheme 1. Illustrated are metallated (e.g. sodium) sulfonated (3a), phosphonated (3b), sulfinated (3c), thiosulfonated (3d), or thiosulfinated (3e) poly(4-vinylbenzene). While not intending to be bound by theory, the sulfur oxoacid anion-substituted and the phosphorus oxoacid anion-substituted polyaromatic resins, where the polyaromatic resin further comprises associated metal cations, are thought to interact with metalalactone 2 in some fashion, for example to form an adduct of some type, such as one illustrated as intermediate 4. Reaction with the combined sulfonated (3a), phosphonated (3b), sulfinated (3c), thiosulfonated (3d), or thiosulfinated (3e) poly(4-vinylbenzene) and metalalactone 2 (or intermediate of some type, represented generally as 4) proceeds to eliminate or release the metal acrylate 6, for example, from adduct 4, and regenerates catalyst compound 1 and byproduct neutral polymer 5, namely, the corresponding sulfur oxoacid-substituted or the phosphorus oxoacid-substituted polyaromatic resin, illustrated as 5a-5d, which are regenerated to the sulfur oxoacid anion-substituted polyaromatic resin or the phosphorus oxoacid anion-substituted polyaromatic resin 3a-3d, upon its reaction with the base 7. Reference to the "neutral" polymers 5 is intended to reflect that the anionic form of the polymer has been partially or largely converted back to the acid form, regardless of whether the polymer 5 is completely neutral in charge. The participation of the polar solvent and/or base in the elimination or release of the metal acrylate 6, is not fully understood at this time and may include direct participation in the mechanism or simply solvating an acrylate salt which is insoluble in the diluent.

As illustrated, the oxoacid-substituted resins such as the sulfonic acid-, phosphonic acid-, sulfinic acid-, thiosulfonic acid-, or thiosulfinic acid-substituted aromatic resins can be regenerated to the anionic (salt) form reactant, for example poly(sodium 4-vinylbenzenesulfonate) 3a, poly(sodium (4-vinylbenzene)phosphonate) 3b, poly(sodium 4-vinylbenzenesulfinate) 3c, poly(sodium 4-vinylbenzenethiosulfonate) 3d, and poly(sodium 4-vinylbenzenethiosulfinate) 3e, upon their respective reactions with the base 7. In other words, elimination of the metal acrylate, for example from intermediate 4, occurs to regenerate catalyst compound 1 and byproduct acid form polymer, as shown in Scheme 1, which can be regenerated to the anionic salt form reactant upon reaction of these acid form polymers with a base 7. In the presence of additional ethylene and $CO_2$, catalyst 1 is converted to metalalactone 2.

Therefore, in an aspect, the sulfur oxoacid anion-substituted polyaromatic resin or the phosphorus oxoacid anion-substituted polyaromatic resin of this disclosure can comprise a sulfonated polyaromatic resin, a phosphonated polyaromatic resin, a sulfinated polyaromatic resin, a thiosulfonated polyaromatic resin, or a thiosulfinated polyaromatic resin. For example, the sulfur oxoacid anion-substituted polyaromatic resin or the phosphorus oxoacid anion-substituted polyaromatic resin can comprise a sulfonated-, a phosphonated-, a sulfinated-, a thiosulfonated-, or a thiosulfinated-styrene polymer or copolymer, such as for example, a styrene-divinylarene copolymer including a styrene-divinylbenzene copolymer. Moreover, the sulfur oxoacid anion-substituted polyaromatic resin or the phosphorus oxoacid anion-substituted polyaromatic resin can be macroreticular. In this aspect, the sulfur oxoacid anion-substituted polyaromatic resin or the phosphorus oxoacid anion-substituted polyaromatic resin has an average particle size from about 0.1 mm to about 1.0 mm, or an average particle size from about 0.50 mm to about 0.80 mm. In an aspect, the average or median particle size is measured by either dynamic light scattering tests or by a laser diffraction technique. Examples of suitable sulfur oxoacid anion-substituted polyaromatic resin include the commercial AMBERLITE® or AMBERLYST® resins.

One exemplary base illustrated in Scheme 1 is a hydroxide base, but a carbonate base, similar inorganic bases, and a wide range of other bases can be used, particularly metal-containing bases. Metal containing bases can include any basic inorganic metal compound or mixture of compounds that contain metal cations or cation sources, for example, alkali and alkaline earth metal compounds such as oxides, hydroxides, alkoxides, aryloxides, amides, alkyl amides, arylamides, and carbonates like calcium hydroxide. In an aspect, the reaction of Scheme 1 can be conducted using certain bases as disclosed, but if desired, other organic bases such as some alkoxide, aryloxide, amide, alkyl amide, arylamide bases, or the like can be excluded. Typically, the inorganic bases such as alkali metal hydroxides have been found to work well.

Generally, the sulfur oxoacid anion-substituted polyaromatic resin or the phosphorus oxoacid anion-substituted polyaromatic resin ("anionic polyelectrolyte") further comprise associated metal cations used in the processes disclosed herein can comprise (or consist essentially of, or consist of) an insoluble anionic polyelectrolyte, a soluble anionic polyelectrolyte, or a combination thereof. That is, the anionic polyelectrolyte material can be soluble, insoluble, or only partially or slightly soluble in the diluent or reaction mixture. It is further contemplated that mixtures or combinations of two or more anionic polyelectrolytes can be employed in certain aspects of the disclosure. Therefore, the "anionic polyelectrolyte" is a polymeric material which comprises a multiply-charged polyanion, together with an equivalent amount of counter cations, and is used generally to refer to both soluble materials and insoluble materials.

In an aspect, the sulfur oxoacid anion-substituted polyaromatic resin or the phosphorus oxoacid anion-substituted polyaromatic resin; wherein the polyaromatic resin further comprises associated metal cations can be used in the absence of an alkoxide or aryloxide base. Further, the reactions and processes disclosed herein can be conducted in the absence of an alkoxide, an aryloxide, an alkylamide, an arylamide, and/or substituted analogs thereof. That is, additional bases with their associated counter ions are not required to effect the processes disclosed herein.

According to an aspect, the sulfur oxoacid anion-substituted polyaromatic resin or the phosphorus oxoacid anion-substituted polyaromatic resin; wherein the polyaromatic resin further comprises associated metal cations can be used in the absence of a solid support. That is the sulfur oxoacid anion-substituted polyaromatic resin or the phosphorus oxoacid anion-substituted polyaromatic resin; wherein the polyaromatic resin further comprises associated metal cations can be used in its natural polymeric form without being bonded to or supported on any insoluble support, such as an inorganic oxide or mixed oxide material.

In an aspect, the term anionic polyelectrolyte is used herein to refer to and include such polyelectrolytes that include sulfur oxoacid anion-substituted material or the phosphorus oxoacid anion-substituted material; wherein the anion-substituted materials further comprise associated metal cations. Examples of associated metal cations can include, but are not limited to, alkali metal cation, alkaline earth cation, or metal cations having varying Lewis acidities. Accordingly, the anionic polyelectrolytes generally include materials such as a poly(styrene sulfonate) (e.g. 3a of Scheme 1), a poly(styrene phosphonate) (e.g. 3b of Scheme 1), a poly(styrene sulfinate) (e.g. 3c of Scheme 1), a poly(styrene thiosulfonate) (e.g. 3d of Scheme 1), a poly(styrene thiosulfinate) (e.g. 3e of Scheme 1), including copolymers of these styrenes with other comonomers. Further, the anionic polyelectrolytes of this disclosure also generally include sulfonated-, phosphonated-, sulfinated-, thiosulfonated-, or thiosulfinated-resins such as phenol-formaldehyde resins, a polyhydroxyarene-formaldehyde resin (such as a resorcinol-formaldehyde resin), a polyhydroxyarene- and fluorophenol-formaldehyde resin (such as a resorcinol- and 2-fluorophenol-formaldehyde resin), and similar materials, along with associated metal cations. Polymers that generally fall under the phenol-formaldehyde type of crosslinked resins may be referred to as polyaromatic resins. Co-polymers of these specific types of anionic polyelectrolytes are also included in this disclosure. The polyelectrolyte core structure can be substituted on the polymer backbone or the pendant groups with sulfur or phosphorus oxoacids (acid form) or anions (salt form) oxoacid anions. Moreover, substituted variations of these polymers are included in the term anionic polyelectrolyte. For example, any of the anionic polyelectrolytes can be substituted with electron-withdrawing groups or electron-donating groups or even combinations thereof.

Anionic polyelectrolytes such as those used herein include associated cations, particularly associated metal cations, including Lewis acidic metal cations and cations with low Lewis acidity. According to an aspect, the associated metal cations can be an alkali metal, an alkaline earth metal, or any combination thereof. Typical associated metal cations can be, can comprise, or can be selected from lithium, sodium, potassium, rubidium, cesium, magnesium, calcium, strontium, barium, zinc, aluminum or gallium and the like. Generally, sodium or potassium associated metal cations have been found to work well. Therefore, cations with a range of Lewis acidities in the particular solvent can be useful according to this disclosure.

One aspect of the disclosed process provides for using a sulfur oxoacid anion-substituted polyaromatic resin or a phosphorus oxoacid anion-substituted polyaromatic resin. In an aspect, the sulfur oxoacid anion-substituted polyaromatic resin or the phosphorus oxoacid anion-substituted polyaromatic resin can comprise, consist essentially of, or consist of: a sodium vinylbenzenesulfonate polymer or copolymer, such as a sodium 4-vinylbenzenesulfonate polymer or copolymer; a sodium vinylphenylphosphonate polymer or copolymer, such as a sodium (4-vinylphenyl)phosphonate polymer or copolymer; a sodium vinylbenzenesulfinate polymer or copolymer, such as a sodium 4-vinylbenzenesulfinate polymer or copolymer; a sodium vinylbenzenethiosulfonate polymer or copolymer, such as a sodium 4-vinylbenzenethiosulfonate polymer or copolymer; and/or a sodium vinylbenzenethiosulfinate polymer or copolymer, such as a sodium 4-vinylbenzenethiosulfinate polymer or copolymer. According to an aspect, the comonomer in these copolymers can be a divinylbenzene, such as a 1,3-divinylbenzene or a 1,4-divinylbenzene. Moreover, associated metal cations other than sodium can be employed in the salt forms of the sulfur oxoacid anion-substituted polyaromatic resin or the phosphorus oxoacid anion-substituted polyaromatic resins, such as, for example, lithium, sodium, potassium, rubidium, cesium, magnesium, calcium, strontium, barium, zinc, aluminum or gallium, and the like.

In a further aspect, useful anionic polyelectrolytes can include phenol-formaldehyde resins, which are cross-linked materials derived from the condensation reaction of phenol with formaldehyde, that are treated with a base or a metal cation source. Advantages of using treated phenol-formaldehyde resins include their insolubility, which allows the use of a range of solvents with these materials, and their relatively high phenol concentration that can be functionalized using a metal base such as an alkali metal hydroxide. An early version of the thermosetting phenol formaldehyde resins formed from the condensation reaction of phenol with formaldehyde is Bakelite™, and various phenol-formaldehyde resins used herein may be referred to generically as "Bakelite" resins. In the context of this disclosure, the use of terms such as Bakelite or general terms such as phenol-formaldehyde resins contemplates that these materials will be treated with a metal-containing base or a metal cation source such as sodium hydroxide prior to their use in the processes disclosed.

In an aspect, the sulfur oxoacid anion-substituted polyaromatic resin or the phosphorus oxoacid anion-substituted polyaromatic resin can be macroporous, that is, can have an average pore diameter greater than about 50 nm. For example, the sulfur oxoacid anion-substituted polyaromatic resin or the phosphorus oxoacid anion-substituted polyaromatic resin can have an average pore diameter from about 50 nm to about 250 nm. Surface area, pore diameter, and pore volume were measured by Brunauer, Emmett and Teller (BET) technique with nitrogen gas used as the probe.

In an aspect, the sulfonated polyaromatic resin can be generated by sulfuric acid treatment of a crosslinked polystyrene or a porous carbonaceous material derived from the pyrolysis of a phenol formaldehyde resin. Similarly, in another aspect, other sulfur oxoacid anion-substituted polyaromatic resins such as the sulfinated polyaromatic resin can generated by $SO_2$ treatment (e.g. $SO_2$(aq), commonly termed sulfurous acid), sulfonic acid treatment, or sulfinic acid treatment of a crosslinked polystyrene or a porous carbonaceous material derived from the pyrolysis of a phenol formaldehyde resin. The thiosulfonated and thiosulfinated polyaromatic resin can generated by, for example, thiosulfonic acid treatment or thiosulfinic acid treatment of a crosslinked polystyrene or a porous carbonaceous material derived from the pyrolysis of a phenol formaldehyde resin. According to another aspect, the phosphonated polyaromatic resin can be formed by aromatic substitution with a chlorinated phosphine, followed by alcoholic or aqueous workup, of a crosslinked polystyrene or a porous carbonaceous material derived from the pyrolysis of a phenol formaldehyde resin.

Other useful anionic polyelectrolytes include substituted phenol-formaldehyde resins that are also generally cross-linked into insoluble resins. These resins can be formed from the condensation reaction of one or more of phenol, a polyhydroxyarene such as resorcinol (also, benzenediol or m-dihydroxybenzene), and/or their substituted analogs with formaldehyde. Therefore, these materials include resins made with more than one phenol as co-monomer. These polymeric materials also can be sulfonated, phosphonated, sulfinated, thiosulfonated, or thiosufinated with the corresponding or suitable acid treatment. Subsequent treatment with bases such as NaOH or KOH also provides a ready method of functionalizing the polyaromatic polymers for the reactivity described herein. In one example, a resin can be prepared using the monomer combination of resorcinol (m-dihydroxybenzene) and fluorophenol monomers with formaldehyde, and these polymeric materials also can be sulfonated, phosphonated, sulfinated, thiosulfonated, or thiosufinated with the corresponding or suitable acid treatment.

For example, sulfonation and phosphonation of aromatic materials can be performed by a treatment of the resin with the appropriate acid under various temperatures, concentrations, and diluent conditions. These oxoacid installations can be accelerated and selectively placed when sulfonated/halogenated aromatic substrates catalytically coupled with sulfonate/phosphonate precursors. For example, alkyl phosphites can be installed and subsequently hydrolyzed when a cross coupling catalyst such as nickel(II) chloride or bromide is employed. Sulfination of an aryl group can occur by reducing the appropriate sulfonyl chloride (prepared from thionyl chloride treatment of the sulfonate) with a reagent such as zinc dust, and also can occur using Grignard reagents, dialkyl zinc compounds, hydrogen/palladium catalyst systems, sodium/mercury amalgam, and other electron sources. Various approaches are described in Chem. Rev., 1951, 48 (1), pp 69-124, which is incorporated herein by reference in its entirety. Thiosulfination and thiosulfonation can proceed from a variety of routes. For example, one utilized protocol involves the oxidative cleavage of disulfide linkages (introduced through sulfur-induced crosslinking of a polyaromatic microstructure), which can be performed using oxidation treatments of various strengths (depending on whether thiosulfinate or thiosulfonate functionality is desired) including mCPBA, hydrogen peroxide, or sulfuryl chloride. Thionyl chloride treatment of such linkages can produce sulfinyl chloride moieties which can be further treated with sodium sulfide or acid to afford the desired material. Subsequent base (e.g. sodium hydroxide or sodium chloride) treatment can be used to generate the metal-stabilized anionic polyelectrolyte. Various approaches to these materials can be found in, for example, Fischmann, A. J.; Spiccia, L. Dalton Trans. 2011, 40, 12310, which is incorporated herein by reference in its entirety.

In those aspects and embodiments in which polymer support variations are used and/or in which the polyelectrolyte itself is a solid that is insoluble in the diluent of the reaction, such solid state polyelectrolyte embodiments can have any suitable surface area, pore volume, and particle size, as would be recognized by those of skill in the art. For instance, the solid polyelectrolyte can have a pore volume in a range from 0.1 to 2.5 mL/g, or alternatively, from 0.5 to 2.5 mL/g. In a further aspect, the solid polyelectrolyte can have a pore volume from 1 to 2.5 mL/g. Alternatively, the pore volume can be from 0.1 to 1.0 mL/g. Additionally, or alternatively, the solid polyelectrolyte can have a surface area in a range from 10 to 750 m$^2$/g; alternatively, from 100 to 750 m$^2$/g; or alternatively, from 100 to 500 m$^2$/g or alternatively from 30 to 200 m$^2$/g. In a further aspect, the solid polyelectrolyte can have a surface area of from 100 to 400 m$^2$/g, from 200 to 450 m$^2$/g, or from 150 to 350 m$^2$/g. The average particle size of the solid polyelectrolyte can vary greatly depending upon the process specifics, however, average particle sizes in the range of from 5 to 500 μm, from 10 to 250 μm, or from 25 to 200 μm, are often employed. Alternatively, ⅛ inch (3.2 mm) to ¼ inch (6.4 mm) pellets or used. Surface area, pore diameter, and pore volume were measured by Brunauer, Emmett and Teller (BET) technique with nitrogen gas used as the probe.

The present disclosure also provides for various modifications of the polymeric anionic stationary phase (anionic polyelectrolytes), for example, in a column or other suitable solid state configuration. Further various modifications of the polymeric anionic stationary phase (anionic polyelectrolytes), for example, in a column or other suitable solid state configuration are useful in the processes disclosed herein. For example, acid-base reactions that generate the anionic polyelectrolyte from the acid form of the polymer can be effected using a wide range of metal bases, including alkali and alkaline hydroxides, alkoxides, aryloxides, amides, alkyl or aryl amides, and the like, such that an assortment of electrophiles can be used in nickelalactone destabilization as demonstrated herein for the poly(vinylbenzenesulfonic acid) and poly(vinylbenzenephosphonic acid).

Polymer modifications can also include using variants of the sulfur oxoacid anion-substituted polyaromatic resin or the phosphorus oxoacid anion-substituted polyaromatic resins, for example, by preparing various poly(vinylbenzene) polymers substituted with an oxyacid of sulfur or an oxyacid of phosphorus. As an example, various styrenes substituted with a protected oxyacid of sulfur or a protected oxyacid of phosphorus and having a variety of organic and inorganic substituents, such as alkyls, halogens, and heteroatom substituents, can be polymerized, and subjected to hydrolysis or acidolysis. Such adjustments can provide flexibility for tailoring the reaction according to the specific olefin to be coupled with $CO_2$, the reaction rate, the catalytic turnover, as well as additional reaction parameters and combinations of reaction parameters.

In a further aspect, polymer modifications can also include using co-polymers based on, for example, the co-polymerization of a protected oxoacid-substituted styrene with other monomers (e.g., styrenes and/or (meth)acrylates) to produce libraries of polymeric electrophiles. Such a library can be utilized to test and match the specific anionic polyelectrolyte with the specific olefin, to improve or optimize reaction rate, catalytic turnover, reaction selectivity, and the like. Further polymer support variations can also be used, for example, polymers can be supported onto beads or other surfaces. Alternatively, one class of polymer support variation that is possible for use with this technology is the cast polymer that can function as an ion exchange membrane. Alternatively, the anionic polyelectrolyte can be unsupported and used in the absence of any support.

Referring again to Scheme 1, the reaction with the combined sulfonated (3a), phosphonated (3b), sulfinated (3c), thiosulfonated (3d), or thiosulfinated (3e) poly(4-vinylbenzene) and metalalactone 2 (or intermediate of some type, represented generally as 4) proceeds to eliminate or release the metal acrylate 6, for example, from adduct 4, and regenerates catalyst compound 1 and byproduct neutral polymer 5a-5e, the corresponding sulfur oxoacid-substituted or the phosphorus oxoacid-substituted polyaromatic resin. These acid-form resins 5a-5e can be regenerated to the sulfur oxoacid anion-substituted polyaromatic resin or the phosphorus oxoacid anion-substituted polyaromatic resin 3a-3e, upon reaction with the base, such as the metal-containing base shown as 7 in Scheme 1. For example, the metal in a metal-containing base can be, but is not limited to, a metal of Groups 1, 2, 12 or 13, such as lithium, sodium, potassium, rubidium, cesium, magnesium, calcium, strontium, barium, zinc, aluminum, or gallium.

The step of regenerating the anionic polyelectrolyte can be effected by contacting the anionic polyelectrolyte with a regenerative base 7 comprising a metal cation following the formation of the α,β-unsaturated carboxylic acid or a salt thereof. A wide range of bases 7 can be used for this regeneration step. For example, the regenerative base 7 can be or can comprise metal-containing bases which can include any reactive inorganic basic metal compound or mixture of compounds that contain metal cations or cation sources, for example, alkali and alkaline earth metal compounds such as oxides, hydroxides, alkoxides, aryloxides, amides, alkyl amides, arylamides, and carbonates. Suitable bases include or comprise, for example, carbonates (e.g., $Na_2CO_3$, $Cs_2CO_3$, $MgCO_3$), hydroxides (e.g., $Mg(OH)_2$, $Ca(OH)_2$, NaOH, KOH), alkoxides (e.g., $Al(O^iPr)_3$, $Na(O^tBu)$, $Mg(OEt)_2$), aryloxides (e.g. $Na(OC_6H_5)$, sodium phenoxide), sulfates (e.g. $Na_2SO_4$, $K_2SO_4$, $CaSO_4$, $MgSO_4$), and the like. In an aspect, certain sulfur oxoacid-substituted polyaromatic resins or a phosphorus oxoacid-substituted polyaromatic resins with particularly acidic groups can be regenerated to the corresponding sulfur oxoacid anion-substituted polyaromatic resin or the phosphorus oxoacid anion-substituted polyaromatic resin upon their reaction with only a metal-containing salt such as sodium chloride. As an example, such resins can have electron-withdrawing substituents situated ortho or para to the sulfur oxoacid functional group or phosphorus oxoacid functional group on a polyaromatic resin, such that the anionic form can readily form and only a metal-containing salt (or "metal salt") such as sodium chloride is required to regenerate the corresponding oxoacid anion-substituted polyaromatic resin. Typically, this regeneration step further comprises or is followed by the step of washing the oxoacid anion-substituted polyaromatic resin with a solvent or the diluent.

In one aspect, the step of regenerating the sulfur oxoacid anion-substituted polyaromatic resin or the phosphorus oxoacid anion-substituted polyaromatic resin can be carried out by contacting a by-product resin that is generated from the process with an aqueous sodium ion ($Na^+$) source, for example, aqueous sodium halide (brine). In an aspect, the step of regenerating the sulfur oxoacid anion-substituted polyaromatic resin or the phosphorus oxoacid anion-substituted polyaromatic resin can be effected by contacting a by-product resin that is generated from the process with an aqueous acid and an aqueous brine, for example, by contacting the by-product resin with aqueous acid followed by aqueous brine, or by contacting the by-product resin with aqueous acid and aqueous brine at the same time. A wash step (e.g. aqueous) can be used, for example, when the by-product resin is contacted with aqueous acid it can be washed with water prior to contacting with aqueous brine. The aqueous brine solution is not limited by concentration, for example, the aqueous solution can contain about 5 wt % to about 15 wt % sodium chloride.

According to an aspect, the regenerative base can be or can comprise a nucleophilic base, for example a metal hydroxide or metal alkoxide. While the regenerative base can comprise a non-nucleophilic base, the processes disclosed herein work in the absence of a non-nucleophilic base such an alkali metal hydride or an alkaline earth metal hydride, an alkali metal or alkaline earth metal dialkylamides and diarylamides, an alkali metal or alkaline earth metal hexalkyldisilazane, and an alkali metal or alkaline earth metal dialkylphosphides and diarylphosphides.

Typically, the inorganic bases such as alkali metal hydroxides or alkali metal alkoxides have been found to work the best. However, in one aspect, the reaction of Scheme 1 can be conducted using some bases but in the absence of certain other organic bases such as an alkoxide, aryloxide, amide, alkyl amide, arylamide, or the like. In another aspect, the anionic polyelectrolyte (and associated cations) can be used and regenerated in the absence of an alkoxide or aryloxide. Further, the reactions and processes disclosed herein can be conducted in the absence of an alkoxide, an aryloxide, an alkylamide, an arylamide, an amine, a hydride, a phosphazene, and/or substituted analogs thereof. For example, the processes disclosed herein can be conducted in the absence of sodium hydride, an aryloxide salt (such as a sodium aryloxide), an alkoxide salt (such as a sodium tert-butoxide), and/or a phosphazene.

The processes disclosed herein typically are conducted in the presence of a diluent. Mixtures and combinations of diluents can be utilized in these processes. The diluent can comprise, consist essentially of, or consist of, any suitable solvent or any solvent disclosed herein, unless otherwise specified. For example, the diluent can comprise, consist essentially of, or consist of a non-protic solvent, a protic solvent, a non-coordinating solvent, or a coordinating solvent. For instance, in accordance with one aspect of this disclosure, the diluent can comprise a non-protic solvent. Representative and non-limiting examples of non-protic solvents can include tetrahydrofuran (THF), 2,5-$Me_2$THF, acetone, toluene, chlorobenzene, pyridine, carbon dioxide, olefin, and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof.

In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-$Me_2$THF, methanol, acetone, toluene, chlorobenzene, pyridine, anisole, or a combination thereof; alternatively, THF; alternatively, 2,5-$Me_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof; alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-$Me_2$THF, 1,2-dimethoxyethane, 1,4-dioxane, anisole, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

In a further aspect, any of these aforementioned diluents can be excluded from the diluent or diluent mixture. For example, the diluent can be absent a phenol or a substituted phenol, an alcohol or a substituted alcohol, an amine or a substituted amine, water, an ether, an aliphatic hydrocarbon solvent, an aromatic hydrocarbon solvent, an aldehyde or ketone, an ester or amide, and/or absent a halogenated aromatic hydrocarbon, or any substituted analogs of these diluents halogenated analogs, including any of the aforementioned diluents. Therefore, Applicant reserves the right to exclude any of the diluents provided herein.

In all aspects and embodiments disclosed herein, the diluent can include or comprise carbon dioxide, olefin, or combinations thereof. At least a portion of the diluent can comprise the α,β-unsaturated carboxylic acid or the salt thereof, formed in the process.

In this disclosure, the term transition metal precursor, transition metal compound, transition metal catalyst, transition metal precursor compound, carboxylation catalyst, transition metal precursor complex, transition metal-ligand, and similar terms refer to a chemical compound that serves as the precursor to the metalalactone, prior to the coupling of the olefin and carbon dioxide at the metal center of the transition metal precursor compound. Therefore, the metal of the transition metal precursor compound and the metal of the metalalactone are the same. In some aspects, some of the ligands of the transition metal precursor compound carry over and are retained by the metalalactone following the coupling reaction. In other aspects, the transition metal precursor compound loses its existing ligands, referred to herein as first ligands, in presence of additional ligands such as chelating ligands, referred to herein as second ligands, as the metalalactone is formed. Therefore, the metalalactone generally incorporates the second (added) ligand(s), though in some aspects, the metalalactone can comprise the first ligand(s) that were bound in the transition metal precursor compound.

According to an aspect, the transition metal catalyst or compound used in the processes can be used without being immobilized on a solid support. That is the transition metal catalyst can be used is its usual form which is soluble in most useful solvents, without being bonded to or supported on any insoluble support, such as an inorganic oxide or mixed oxide material.

A prototypical example of a transition metal precursor compound that loses its initial ligands in the coupling reaction in the presence of a second (added) ligand, wherein the metalalactone incorporates the second (added) ligand(s), is contacting Ni(COD)$_2$ (COD is 1,5-cyclooctadiene) with a diphosphine ligand such as 1,2-bis(dicyclohexylphosphino)ethane in a diluent in the presence of ethylene and CO$_2$ to form a nickelalactone with a coordinated 1,2-bis(dicyclohexylphosphino)ethane bidentate ligand.

In an aspect, any of the metalalactone ligand (that is, any ligand of the metalalactone compound other than the metalalactone moiety), the first ligand, or the second ligand can comprise at least one of a nitrogen, phosphorus, sulfur, or oxygen heteroatom. For example, any of the metalalactone ligand, the first ligand, or the second ligand comprises or is selected from a diphosphine ligand, a diamine ligand, a diene ligand, a diether ligand or dithioether ligand. According to another aspect, any of the metalalactone ligand, the first ligand, or the second ligand comprises or is selected from a) an asymmetric ligand (comprising different donor atoms) such as 2-pyridylphosphine or b) an N-heterocyclic carbene (NHC) ligand.

Accordingly, in an aspect, the process for producing or forming an α,β-unsaturated carboxylic acid or a salt thereof, can comprise:
  a) contacting in any order
    1) a transition metal precursor compound comprising at least one first ligand;
    2) optionally, at least one second ligand;
    3) an olefin;
    4) carbon dioxide (CO$_2$);
    5) a diluent; and
    6) a sulfur oxoacid anion-substituted polyaromatic resin or a phosphorus oxoacid anion-substituted polyaromatic resin; wherein the polyaromatic resin further comprises associated metal cations to provide a reaction mixture; and
  b) applying reaction conditions to the reaction mixture suitable to form the α,β-unsaturated carboxylic acid or the salt thereof.

Generally, the processes disclosed herein employ a metalalactone or a transition metal precursor compound or complex. The transition metal of the metalalactone, or of the transition metal precursor compound, can be a Group 3 to Group 8 transition metal or, alternatively, a Group 8 to Group 11 transition metal. In one aspect, for instance, the metal of the metalalactone or the metal of the transition metal precursor compound is Cr, Fe, Co, Ni, Cu, Mo, Ru, Rh, Pd, W, Ag, Ir, Pt, or Au, while in another aspect, the transition metal can be Fe, Ni, or Rh. Alternatively, the transition metal can be Cr; alternatively, the transition metal can be Fe; alternatively, the transition metal can be Co; alternatively, the transition metal can be Ni; alternatively, the transition metal can be Cu; alternatively, the transition metal can be Mo; alternatively, the transition metal can be Ru; alternatively, the transition metal can be Rh; alternatively, the transition metal can be Pd; alternatively, the transition metal can be W; alternatively, the transition metal can be Ag; alternatively, the transition metal can be Ir; alternatively, the transition metal can be Pt; or alternatively, the transition metal can Au.

In particular aspects contemplated herein, the transition metal can be Ni. Hence, the metalalactone can be a nickelalactone and the transition metal precursor compound can be a Ni-ligand complex in these aspects.

The ligand of the metalalactone and/or of the transition metal precursor compound, can be any suitable neutral electron donor group and/or Lewis base. For instance, the suitable neutral ligands can include sigma-donor solvents that contain a coordinating atom (or atoms) that can coordinate to the transition metal of the metalalactone (or of the transition metal precursor compound). Examples of suitable coordinating atoms in the ligands can include, but are not limited to, O, N, S, and P, or combinations of these atoms. In some aspects, consistent with this disclosure, the ligand can be a bidentate ligand.

In an aspect, the ligand used to form the metalalactone and/or the transition metal precursor compound can be an ether, an organic carbonyl, a thioether, an amine, a nitrile, or a phosphine. In another aspect, the ligand used to form the metalalactone or the transition metal precursor compound can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophenone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1,8-Diazabicyclo[5.4.0]undec-7-ene, di(2-pyridyl)dimethylsilane, N,N,N',N'-tetramethylethylenediamine, 1,10-phenanthroline, 2,9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-T-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis(dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino)propane, 1,4-bis(diisopropylphosphino)butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis(diphenylphosphino)ferrocene, bis(diphenylphosphino)methane, bis(dicyclohexylphosphino)methane, bis(di-t-butylphosphino)methane, and the like, including substituted derivatives thereof.

In other aspects, the ligand used to form the metalalactone or the transition metal precursor compound can be a carbene, for example, a N-heterocyclic carbene (NHC) compound. Representative and non-limiting examples of suitable N-heterocyclic carbene (NHC) materials include the following:

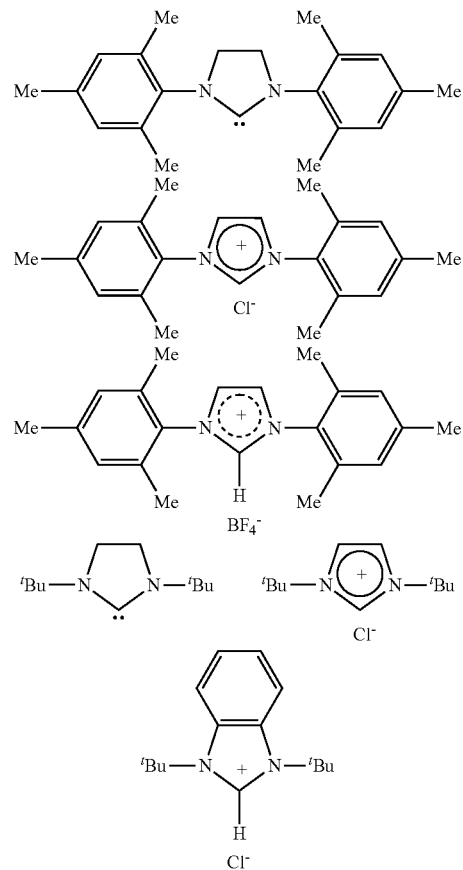

Illustrative and non-limiting examples of metalalactone complexes (representative nickelalactones) suitable for use as described herein include the following compounds (Cy=cyclohexyl, $^t$Bu=tert-butyl):

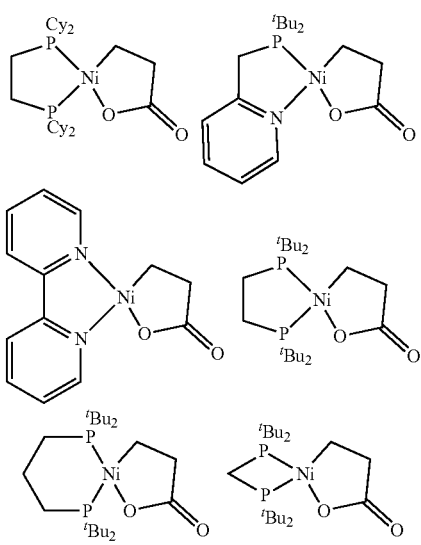

The transition metal precursor compounds corresponding to these illustrative metalalactones are shown below:

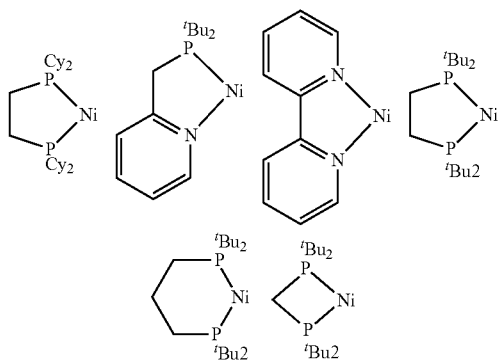

Metalalactones can be synthesized according to the following general reaction scheme (illustrated with nickel as the transition metal; Ni(COD)$_2$ is bis(1,5-cyclooctadiene) nickel(0)), and according to suitable procedures well known to those of skill in the art.

Scheme 2

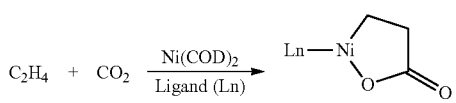

Suitable ligands, transition metal precursor compounds, and metalalactones are not limited solely to those ligands, transition metal precursor compounds, and metalalactones disclosed herein. Other suitable ligands, transition metal precursor compounds, and metalalactones are described, for example, in U.S. Pat. Nos. 7,250,510, 8,642,803, and 8,697,909; Journal of Organometallic Chemistry, 1983, 251, C51-053; Z. Anorg. Allg. Chem., 1989, 577, 111-114; Journal of Organometallic Chemistry, 2004, 689, 2952-2962; Organometallics, 2004, Vol. 23, 5252-5259; Chem. Commun., 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

The following references provide information related to the structure and/or activity relationships in the olefin and CO$_2$ coupling process, as observed by changes in phenoxide structure, the phosphine ligand structure, and other ligand structures: Manzini, S.; Huguet, N.; Trapp, O.; Schaub, T. Eur. J. Org. Chem. 2015, 7122; and Al-Ghamdi, M.; Vummaleti, S. V. C.; Falivene, L.; Pasha, F. A.; Beetstra, D. J.; Cavallo, L. Organometallics 2017, 36, 1107-1112. These references are incorporated herein by reference in their entireties.

Generally, the features of the processes disclosed herein (e.g., the metalalactone, the diluent, the anionic polyelectrolyte, the α,β-unsaturated carboxylic acid or salt thereof, the transition metal precursor compound, the olefin, and the reaction conditions under which the α,β-unsaturated carboxylic acid, or a salt thereof, is formed, among others) are independently described, and these features can be combined in any combination to further describe the disclosed processes.

In accordance with an aspect of the present disclosure, a process for performing a metalalactone elimination reaction is disclosed, in which the process forms an α,β-unsaturated carboxylic acid or salt thereof. This process can comprise (or consist essentially of, or consist of):

a) contacting
1) a metalalactone compound;
2) a diluent; and
3) a sulfur oxoacid anion-substituted polyaromatic resin or a phosphorus oxoacid anion-substituted polyaromatic resin; wherein the polyaromatic resin further comprises associated metal cations to provide a reaction mixture; and b) applying reaction conditions to the reaction mixture suitable to form the α,β-unsaturated carboxylic acid or the salt thereof. For example, the suitable reaction conditions may induce a metalalactone elimination reaction to produce the α,β-unsaturated carboxylic acid or a salt thereof.

Suitable metalalactones, diluents, and sulfur oxoacid anion-substituted polyaromatic resin or phosphorus oxoacid anion-substituted polyaromatic resins (anionic polyelectrolytes) are disclosed hereinabove. In this process for form the α,β-unsaturated carboxylic acid or the salt thereof, for instance, at least a portion of the diluent can comprise the α,β-unsaturated carboxylic acid, or the salt thereof, that is formed in step b) of this process.

In accordance with another aspect of the present disclosure, a process for producing an α,β-unsaturated carboxylic acid, or a salt thereof, is disclosed. This process can comprise (or consist essentially of, or consist of):

a) contacting
1) a metalalactone compound;
2) a diluent; and
3) a sulfur oxoacid anion-substituted polyaromatic resin or a phosphorus oxoacid anion-substituted polyaromatic resin; wherein the polyaromatic resin further comprises associated metal cations, to provide a reaction mixture comprising an adduct of the metalalactone compound and sulfur oxoacid anion-substituted polyaromatic resin or a phosphorus oxoacid anion-substituted polyaromatic resin; and b) applying reaction conditions to the reaction mixture suitable to induce a metalalactone elimination reaction to produce the α,β-unsaturated carboxylic acid or the salt thereof.

In this process for producing an α,β-unsaturated carboxylic acid or a salt thereof, for instance, at least a portion of the diluent of the reaction mixture comprising the adduct of the metalalactone can be removed after step a), and before step b), of this process. Suitable metalalactones, diluents, and sulfur oxoacid anion-substituted polyaromatic resins or phosphorus oxoacid anion-substituted polyaromatic resins (anionic polyelectrolytes) are disclosed hereinabove.

As discussed further in this disclosure, the above processes can further comprise a step of contacting a transition metal precursor compound comprising at least one first ligand, an olefin, and carbon dioxide ($CO_2$) to form the metalalactone compound. That is, at least one ligand of the transition metal precursor compound can be carried over to the metalalactone compound. In further aspects, the above processes can further comprise a step of contacting a transition metal precursor compound comprising at least one first ligand with at least one second ligand, an olefin, and carbon dioxide ($CO_2$) to form the metalalactone compound. In this aspect, the ligand set of the metalalactone typically comprises the at least one ligand in addition to the metalalactone moiety. That is, the metalalactone compound can comprise the at least one first ligand, the at least one second ligand, or a combination thereof.

In some aspects, the contacting step, step a) of the above processes, can include contacting, in any order, the metalalactone, the diluent, and the sulfur oxoacid anion-substituted polyaromatic resin or the phosphorus oxoacid anion-substituted polyaromatic resin, and additional unrecited materials. In other aspects, the contacting step can consist essentially of, or consist of, the metalalactone, the diluent, and the anionic polyelectrolyte components. Likewise, additional materials or features can be employed in the applying reaction conditions step, step b) of the above processes, that forms or produces the α,β-unsaturated carboxylic acid, or the salt thereof. Further, it is contemplated that these processes for producing an α,β-unsaturated carboxylic acid or a salt thereof by a metalalactone elimination reaction can employ more than one metalalactone and/or more than one anionic polyelectrolyte. Additionally, a mixture or combination of two or more diluents can be employed.

Any suitable reactor, vessel, or container can be used to contact the metalalactone, diluent, and anionic polyelectrolyte, non-limiting examples of which can include a flow reactor, a continuous reactor, a fixed bed reactor, a moving reactor bed, a stirred bed reactor, a bubbling bed reactor, and a stirred tank reactor, including more than one reactor in series or in parallel, and including any combination of reactor types and arrangements. In particular aspects consistent with this disclosure, the metalalactone and the diluent can contact a fixed bed of the anionic polyelectrolyte, for instance, in a suitable vessel, such as in a continuous fixed bed reactor. In other aspects, consistent with this disclosure, the metalalactone and the diluent can contact a moving bed of the anionic polyelectrolyte, for instance, in a suitable vessel, such as in a moving reactor bed, a stirred bed reactor, or a bubbling bed reactor. In further aspects, combinations of more than one anionic polyelectrolyte can be used, such as a mixed bed of a first anionic polyelectrolyte and a second anionic polyelectrolyte, or sequential beds of a first anionic polyelectrolyte and a second anionic polyelectrolyte. In still further aspects, the sulfur oxoacid anion-substituted polyaromatic resin or the phosphorus oxoacid anion-substituted polyaromatic resin of the contacting step a) is arranged as a fixed bed, a bubbling bed, a moving bed, or a stirred bed. In these and other aspects, the feed stream can flow upward or downward through the fixed bed. For instance, the metalalactone and the diluent can contact the first anionic polyelectrolyte and then the second anionic polyelectrolyte in a downward flow orientation, and the reverse in an upward flow orientation. In a different aspect, the metalalactone and the anionic polyelectrolyte can be contacted by mixing or stirring in the diluent, for instance, in a suitable vessel, such as a stirred tank reactor.

Step a) of the process for producing an α,β-unsaturated carboxylic acid or a salt thereof also recites forming an adduct of the metalalactone and the sulfur oxoacid anion-substituted polyaromatic resin or the phosphorus oxoacid anion-substituted polyaromatic resin; wherein the polyaromatic resin further comprises associated metal cations. Without intending to be bound by theory, there is some interaction between the metalalactone and the anionic polyelectrolyte and its associated metal cations that are believed to destabilize the metalalactone for its elimination of the metal acrylate. This interaction can be referred to generally as an adduct of the metalalactone and the sulfur oxoacid anion-substituted polyaromatic resin or the phosphorus oxoacid anion-substituted polyaromatic resin (anionic polyelectrolyte) or an adduct of the α,β-unsaturated carboxylic acid with the sulfur oxoacid anion-substituted polyaromatic resin or the phosphorus oxoacid anion-substituted polyaromatic resin. This adduct can contain all or a portion of the α,β-unsaturated carboxylic acid and can be inclusive of salts of the α,β-unsaturated carboxylic acid.

Accordingly, applying reaction conditions to the reaction mixture suitable to form an α,β-unsaturated carboxylic acid or a salt thereof is intended to reflect any concomitant or subsequent conditions to step a) of the above processes that release the α,β-unsaturated carboxylic acid or a salt thereof from the adduct, regardless of the specific nature of the adduct.

For example, in step b) of the process of applying reaction conditions to the reaction mixture suitable to form an α,β-unsaturated carboxylic acid or a salt thereof, the adduct of the metalalactone and the anionic polyelectrolyte and its associated metal cations as defined herein is subjected to some chemical or other conditions or treatment to produce the α,β-unsaturated carboxylic acid or its salt. Various methods can be used to liberate the α,β-unsaturated carboxylic acid or its salt, from the anionic polyelectrolyte. In one aspect, for instance, the treating step can comprise contacting the adduct of the metalalactone and the anionic polyelectrolyte and its associated metal cations with an acid. Representative and non-limiting examples of suitable acids can include HCl, acetic acid, and the like, as well as combinations thereof. In another aspect, the treating step can comprise contacting the adduct of the metalalactone and the anionic polyelectrolyte and its associated metal cations with a base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$, alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the treating step can comprise contacting the adduct of the metalalactone and the anionic polyelectrolyte and its associated metal cations with a suitable solvent. Representative and non-limiting examples of suitable solvents can include carbonyl-containing solvents such as ketones, esters, amides, etc. (e.g., acetone, ethyl acetate, N,N-dimethylformamide, etc., as described herein above), alcohol solvents, water, and the like, as well as combinations thereof.

In still another aspect, the treating step can comprise heating the adduct of the metalalactone and the anionic polyelectrolyte and its associated metal cations to any suitable temperature. This temperature can be in a range, for example, from 50 to 1000° C., from 100 to 800° C., from 150 to 600° C., from 250 to 1000° C., from 250° C. to 550° C., or from 150° C. to 500° C. The duration of this heating step is not limited to any particular period of time, as long of the period of time is sufficient to liberate the α,β-unsaturated carboxylic acid from the anionic polyelectrolyte. As those of skill in the art recognize, the appropriate treating step depends upon several factors, such as the particular diluent used in the process, and the particular anionic polyelectrolyte used in the process, amongst other considerations. One further treatment step can comprise, for example, a workup step with additional olefin to displace an alkene-nickel bound acrylate.

In these processes for performing a metalalactone elimination reaction and for producing an α,β-unsaturated carboxylic acid (or a salt thereof), additional process steps can be conducted before, during, and/or after any of the steps described herein. As an example, these processes can further comprise a step (e.g., prior to step a)) of contacting a transition metal precursor compound with an olefin and carbon dioxide to form the metalalactone. Transition metal precursor compound are described hereinabove. Illustrative and non-limiting examples of suitable olefins can include ethylene, propylene, butene (e.g., 1-butene), pentene, hexene (e.g., 1-hexene), heptane, octene (e.g., 1-octene), and styrene and the like, as well as combinations thereof.

In accordance with another aspect of the present disclosure, a process for forming an α,β-unsaturated carboxylic acid, or a salt thereof, involves coupling an olefin with carbon dioxide, in the present of a transition metal precursor compound. For example, this process or method can comprise (or consist essentially of, or consist of):

a) contacting in any order
1) a transition metal precursor compound comprising at least one first ligand;
2) optionally, at least one second ligand;
3) an olefin;
4) carbon dioxide ($CO_2$);
5) a diluent; and
6) a sulfur oxoacid anion-substituted polyaromatic resin or a phosphorus oxoacid anion-substituted polyaromatic resin; wherein the polyaromatic resin further comprises associated metal cations to provide a reaction mixture; and
b) applying reaction conditions to the reaction mixture suitable to form the α,β-unsaturated carboxylic acid or the salt thereof.

In aspects of this process that utilizes a transition metal precursor compound comprising at least one first ligand, the olefin can be ethylene, and the step of contacting a transition metal precursor compound with an olefin and carbon dioxide ($CO_2$) can be conducted using any suitable pressure of ethylene, or any pressure of ethylene disclosed herein, e.g., from 10 psig (70 KPa) to 1,000 psig (6,895 KPa), from 25 psig (172 KPa) to 500 psig (3,447 KPa), or from 50 psig (345 KPa) to 300 psig (2,068 KPa), and the like. Further, the olefin can be ethylene, and the step of contacting a transition metal precursor compound with an olefin and carbon dioxide ($CO_2$) can be conducted using a constant addition of the olefin, a constant addition of carbon dioxide, or a constant addition of both the olefin and carbon dioxide, to provide the reaction mixture. By way of example, in a process wherein the ethylene and carbon dioxide ($CO_2$) are constantly added, the process can utilize an ethylene:$CO_2$ molar ratio of from 5:1 to 1:5, from 3:1 to 1:3, from 2:1 to 1:2, or about 1:1, to provide the reaction mixture.

According to a further aspect of the above process that utilizes a transition metal precursor compound, the process can include the step of contacting a transition metal precursor compound with an olefin and carbon dioxide ($CO_2$) conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), and the like. In any of the processes disclosed herein, the processes can further comprise a step of monitoring the concentration of at least one reaction mixture component, at least one elimination reaction product, or a combination thereof, for any reason, such as to adjust process parameters in real time, to determine extent or reaction, or to stop the reaction at the desired point.

As illustrated, this process that utilizes a transition metal precursor compound comprising at least one first ligand includes one aspect in which no second ligand is employed in the contacting step, and another aspect in which a second ligand is used in the contacting step. That is, one aspect involves the contacting step of the process comprising contacting the transition metal precursor compound comprising at least one first ligand with the at least one second ligand. The order of contacting can be varied. For example, the contacting step of the process disclosed above can comprise contacting 1) the transition metal precursor compound comprising at least one first ligand with 2) the at least one second ligand to form a pre-contacted mixture, followed by contacting the pre-contacted mixture with the remaining components 3)-6) in any order to provide the reaction mixture.

Further embodiments related to the order of contacting, for example, the contacting step can include or comprise contacting the metalalactone, the diluent, and the sulfur oxoacid anion-substituted polyaromatic resin or the phosphorus oxoacid anion-substituted polyaromatic resin (anionic polyelectrolyte) in any order. The contacting step can also comprise contacting the metalalactone and the diluent to form a first mixture, followed by contacting the first mixture with the anionic polyelectrolyte to form the reaction mixture. In a further aspect, the contacting step can comprise contacting the diluent and the anionic polyelectrolyte to form a first mixture, followed by contacting the first mixture with the metalalactone to form the reaction mixture. In yet a further aspect, the contacting step of the process further comprises contacting any number of additives, for example, additives that can be selected from an acid, a base, or a reductant.

Suitable transition metal precursors, first ligands, second ligands, olefins, diluents, anionic polyelectrolytes with associated metal cations are disclosed hereinabove. In some aspects, the contacting step—step a)—of this process can include contacting, in any order, the transition metal-ligand, the olefin, the diluent, the anionic polyelectrolyte, and carbon dioxide, and additional unrecited materials. In other aspects, the contacting step can consist essentially of, or consist of, contacting, in any order, the transition metal-ligand, the olefin, the diluent, the anionic polyelectrolyte, and carbon dioxide. Likewise, additional materials or features can be employed in the forming step of step b) of this process. Further, it is contemplated that this processes for producing an α,β-unsaturated carboxylic acid, or a salt thereof, can employ more than one transition metal-ligand complex and/or more than one anionic polyelectrolyte if desired and/or more than one olefin. Additionally, a mixture or combination of two or more diluents can be employed.

As above, any suitable reactor, vessel, or container can be used to contact the transition metal precursors, first ligands, second ligands, olefin, diluent, anionic polyelectrolyte, and carbon dioxide, whether using a fixed bed of the anionic polyelectrolyte, a stirred tank for contacting (or mixing), or some other reactor configuration and process. While not wishing to be bound by the following theory, a proposed and illustrative reaction scheme for this process is provided below.

Scheme 3

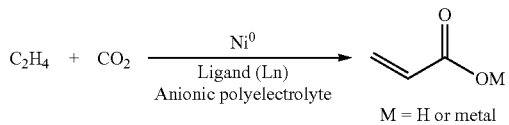

Independently, the contacting and forming steps of any of the processes disclosed herein (i.e., for performing a metalalactone elimination reaction, for producing an α,β-unsaturated carboxylic acid, or a salt thereof), can be conducted at a variety of temperatures, pressures, and time periods. For instance, the temperature at which the components in step a) are initially contacted can be the same as, or different from, the temperature at which the forming step b) is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein can be conducted at a temperature in a range from 0° C. to 250° C.; alternatively, from 20° C. to 200° C.; alternatively, from 0° C. to 95° C.; alternatively, from 10° C. to 75° C.; alternatively, from 10° C. to 50° C.; or alternatively, from 15° C. to 70° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, the contacting step and/or the forming step of the processes disclosed herein can be conducted at a pressure in a range from 5 (34 KPa) to 10,000 psig (68,948 KPa), such as, for example, from 5 psig (34 KPa) to 2500 psig (17,237 KPa). In some aspects, the pressure can be in a range from 5 psig (34 KPa) to 500 psig (3,447 KPa); alternatively, from 25 psig (172 KPa) to 3000 psig (20,684 KPa); alternatively, from 45 psig (310 KPa) to 1000 psig (6,895 KPa); or alternatively, from 50 psig (345 KPa) to 250 psig (1,724 KPa).

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process employed is a continuous process, then the metalalactone/anionic electrolyte catalyst contact/reaction time (or the transition metal precursors, first ligands, second ligands, olefin, diluent, anionic polyelectrolyte, and carbon dioxide contact/reaction time) can be expressed in terms of weight hourly space velocity (WHSV)—the ratio of the weight of the metalalactone (or the solution continuing the transition metal precursors, first ligands, second ligands, olefin, diluent, anionic polyelectrolyte, and carbon dioxide) which comes in contact with a given weight of anionic electrolyte per unit time (for example, $hr^{-1}$). While not limited thereto, the WHSV employed, based on the amount of the anionic electrolyte, can be in a range from 0.05 to 100 $hr^{-1}$, from 0.05 to 50 $hr^{-1}$, from 0.075 to 50 $hr^{-1}$, from 0.1 to 25 $hr^{-1}$, from 0.5 to 10 $hr^{-1}$, from 1 to 25 $hr^{-1}$, or from 1 to 5 $hr^{-1}$.

In the processes disclosed herein, the molar yield of the α,β-unsaturated carboxylic acid, or the salt thereof), based on the metalalactone (or the metal precursors) is at least 2%, and more often can be at least 5%, at least 10%, or at least 15%. In particular aspects of this disclosure, the molar yield can be at least 18%, at least 20%, at least 25%, at least 35%, at least 50%, at least 60%, at least 75%, or at least 85%, or at least 90%, or at least 95%, or at least 100%. That is, catalytic formation of the α,β-unsaturated carboxylic acid or the salt thereof can be effected with the disclosed system. For example, the molar yield of the α,β-unsaturated carboxylic acid, or the salt thereof, based on the metalalactone or based on the transition metal precursor compound can be at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%.

The specific α,β-unsaturated carboxylic acid (or salt thereof) that can be formed or produced using the processes of this disclosure is not particularly limited. Illustrative and non-limiting examples of the α,β-unsaturated carboxylic acid can include acrylic acid, methacrylic acid, 2-ethylacrylic acid, cinnamic acid, and the like, as well as combinations thereof. Illustrative and non-limiting examples of the salt of the α,β-unsaturated carboxylic acid can include sodium acrylate, potassium acrylate, magnesium acrylate, sodium (meth)acrylate, and the like, as well as combinations thereof.

Once formed, the α,β-unsaturated carboxylic acid (or salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process can for performing a metalalactone elimination reaction (or the process for producing an α,β-unsaturated carboxylic acid, or a salt thereof) can further comprise a step of separating or isolating the α,β-unsaturated carboxylic acid (or salt thereof) from other components, e.g., the diluent, the anionic electrolyte, and the like.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

General Considerations

Unless otherwise noted, all operations were performed under purified nitrogen or vacuum using standard Schlenk or glovebox techniques. Toluene (Honeywell) and tetrahydrofuran (Aldrich) was degassed and dried over activated 4 Å molecular sieves under nitrogen. Sodium tert-butoxide, potassium tert-butoxide, poly(4-vinylbenzenesulfonic acid) and poly(4-vinylbenzenephosphonic acid), were prepared by published methods or purchased from Sigma-Aldrich and used as received.

Phenol/formaldehyde resin was purchased as hollow beads (~5-127 μm) from Polysciences, Inc. Bis(1,5-cyclooctadiene)nickel(0) and 1,2-bis(dicyclohexylphosphino)ethane were purchased from Strem and were used as received. (TMEDA)Ni(CH$_2$CH$_2$CO$_2$) was prepared according to literature procedures (Fischer, R; Nestler, B., and Schutz, H. Z. anorg. allg. Chem. 577 (1989) 111-114).

Preparation of Compounds

Sodium phenol/formaldehyde resin. Phenolic resin (phenol/formaldehyde resin) was suspended in a solution of sodium hydroxide in either water or methanol and stirred at 55° C. overnight prior to filtration, and subsequently washed with copious amounts of the solvent in which it was treated. The solid was then dried under vacuum prior to storage under nitrogen.

Preparation of functionalized polyaromatic resins. The sulfur oxoacid anion-substituted polyaromatic resins and/or a phosphorus oxoacid anion-substituted polyaromatic resins can be prepared as disclosed hereinabove. For example, sulfonation and phosphonation of aromatic materials can be performed by a treatment of the resin with the appropriate acid under various temperatures, concentrations, and diluent conditions. These oxoacid installations can be accelerated and selectively placed when sulfonated/halogenated aromatic substrates catalytically coupled with sulfonate/phosphonate precursors. For example, alkyl phosphites can be installed and subsequently hydrolyzed when a cross coupling catalyst such as nickel(II) chloride or bromide is employed. Sulfination of an aryl group can occur by reducing the appropriate sulfonyl chloride (prepared from thionyl chloride treatment of the sulfonate) with a reagent such as zinc dust, and also can occur using Grignard reagents, dialkyl zinc compounds, hydrogen/palladium catalyst systems, sodium/mercury amalgam, and other electron sources. Various approaches are described in Chem. Rev., 1951, 48 (1), pp 69-124, which is incorporated herein by reference in its entirety. Thiosulfination and thiosulfonation can proceed from a variety of routes. For example, one utilized protocol involves the oxidative cleavage of disulfide linkages (introduced through sulfur-induced crosslinking of a polyaromatic microstructure), which can be performed using oxidation treatments of various strengths (depending on whether thiosulfinate or thiosulfonate functionality is desired) including mCPBA, hydrogen peroxide, or sulfuryl chloride. Thionyl chloride treatment of such linkages can produce sulfinyl chloride moieties which can be further treated with sodium sulfide or acid to afford the desired material. Subsequent base (e.g. sodium hydroxide or sodium chloride) treatment can be used to generate the metal-stabilized anionic polyelectrolyte. Various approaches to these materials can be found in, for example, Fischmann, A. J.; Spiccia, L. Dalton Trans. 2011, 40, 12310, which is incorporated herein by reference in its entirety.

Examples 1-20

Experimental Procedure for Ethylene/Carbon Dioxide Coupling

The ethylene/carbon dioxide reaction of these examples is set out in Scheme 4 below, and specific reagents, reaction conditions, and yields are set out in Table 1.

A 1-liter autoclave pressure reactor is charged with solvent followed by a combined mixture of Ni(COD)$_2$ (0.10 mmol), bis(dicyclohexylphosphino)ethane (0.11 mmol), and poly(4-vinylbenzenesulfonic acid) or poly(4-vinylbenzenephosphonic acid) (1.00 g) in 10 mL of solvent. The reactor is set to 50° C., pressurized with ethylene at the desired level, and equilibrated for 5-10 minutes (min) prior to being pressurized and equilibrated with carbon dioxide. The reactor is set to 100° C. and is stirred for 6 hours. After this reaction time, and after cooling to ambient temperature, the reactor is slowly vented and the mixture is collected. The solvent is removed in vacuo and the residue is stirred in 10-20 mL of deuterium oxide for 30 min prior to the addition of a sorbic acid/acetone-d$_6$ solution. The mixture can then be filtered and analyzed by NMR (sorbic acid is used as the internal standard) for acrylate yield determination.

Scheme 4

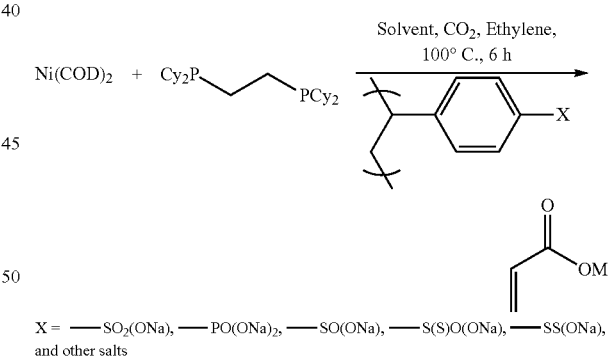

X = ──SO$_2$(ONa), ──PO(ONa)$_2$, ──SO(ONa), ──S(S)O(ONa), ──SS(ONa), and other salts

TABLE 1

Ethylene and carbon dioxide coupling examples

| Example | X | Solvent | [Solvent] (mL) | [C$_2$H$_4$] (psi (KPa)) | [CO$_2$] (psi (KPa)) |
|---|---|---|---|---|---|
| 1 | SO$_2$(ONa) | Toluene | 300 | 100 (689) | 150 (1,034) |
| 2 | PO(ONa)$_2$ | Toluene | 300 | 100 (689) | 150 (1,034) |
| 3 | SO(ONa) | Toluene | 300 | 100 (689) | 150 (1,034) |

TABLE 1-continued

Ethylene and carbon dioxide coupling examples

| Example | X | Solvent | [Solvent] (mL) | [C$_2$H$_4$] (psi (KPa)) | [CO$_2$] (psi (KPa)) |
|---|---|---|---|---|---|
| 4 | S(S)O(ONa) | Toluene | 300 | 100 (689) | 150 (1,034) |
| 5 | SS(ONa) | Toluene | 300 | 100 (689) | 150 (1,034) |
| 6 | SO$_2$(ONa) | Toluene | 100 | 150 (1,034) | 300 (2,068) |
| 7 | PO(ONa)$_2$ | Toluene | 100 | 150 (1,034) | 300 (2,068) |
| 8 | SO(ONa) | Toluene | 100 | 150 (1,034) | 300 (2,068) |
| 9 | S(S)O(ONa) | Toluene | 100 | 150 (1,034) | 300 (2,068) |
| 10 | SS(ONa) | Toluene | 100 | 150 (1,034) | 300 (2,068) |
| 11 | SO$_2$(ONa) | THF | 300 | 75 (517) | 300 (2,068) |
| 12 | PO(ONa)$_2$ | THF | 300 | 75 (517) | 300 (2,068) |
| 13 | SO(ONa) | THF | 300 | 75 (517) | 300 (2,068) |
| 14 | S(S)O(ONa) | THF | 300 | 75 (517) | 300 (2,068) |
| 15 | SS(ONa) | THF | 300 | 75 (517) | 300 (2,068) |
| 16 | SO$_2$(ONa) | Toluene | 50 | 100 (689) | 250 (1,723) |
| 17 | PO(ONa)$_2$ | Toluene | 50 | 100 (689) | 250 (1,723) |
| 18 | SO(ONa) | Toluene | 50 | 100 (689) | 250 (1,723) |
| 19 | S(S)O(ONa) | Toluene | 50 | 100 (689) | 250 (1,723) |
| 20 | SS(ONa) | Toluene | 50 | 100 (689) | 250 (1,723) |

Additional resin types that can be employed according to the reaction Scheme 4 and this disclosure are illustrated in the following reaction Scheme 5, and reaction parameters such as disclosed in the table above can be utilized in this reaction scheme as well.

Scheme 5

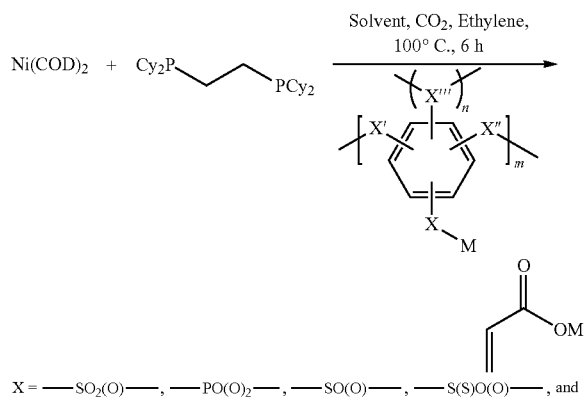

X = ––SO$_2$(O)––, ––PO(O)$_2$––, ––SO(O)––, ––S(S)O(O)––, and
––SS(O)–– and other oxo anion and oxoacid linkages
M = Na, K, Li, Cs, Mg, Cu, and other metals
X′, X″, and X‴ vary according to the resin types disclosed

Examples 21-37

Experimental Procedure for Nickelalactone Conversion to Acrylate

To study the elimination step of the disclosed process, the efficiencies of various alkoxides or aryloxides for the conversion of a diphosphine-stabilized nickelalactone to acrylic acid were assessed. Specifically, the following experiments show the efficiencies of sodium and potassium (4-vinylphenoxide) for the conversion of an in situ prepared diphosphine-stabilized nickelalactone, and the data were compared to the conversion using molecular sodium tert-butoxide for acrylate formation from the analogous nickelalactones. The metalalactone to acrylate conversion reaction of these examples is set out in the scheme below, with exemplary sulfur oxoacid anion-substituted polyaromatic resin or the phosphorus oxoacid anion-substituted polyaromatic resins shown. Additional sulfur oxoacid anion-substituted polyaromatic resin or the phosphorus oxoacid anion-substituted polyaromatic resins are set out in Table 2, along with suitable solvents, that can be used in the process of Scheme 6.

In a 10 mL vial, (TMEDA)Ni(CH$_2$CH$_2$CO$_2$) (0.018 mmol), bis(dicyclohexylphosphino)-ethane (0.018 mmol), the sulfur oxoacid anion-substituted polyaromatic resin or the phosphorus oxoacid anion-substituted polyaromatic resin, and solvent (5 mL) is combined and stirred at 60° C. for 30-60 min. Following removal of solvent, the solid residue is taken up in D$_2$O (3-5 mL) for 30 min and filtered. An aliquot of a prepared sorbic acid/acetone-d$_6$ solution can be added for determination of acrylic acid yield by NMR.

Scheme 6

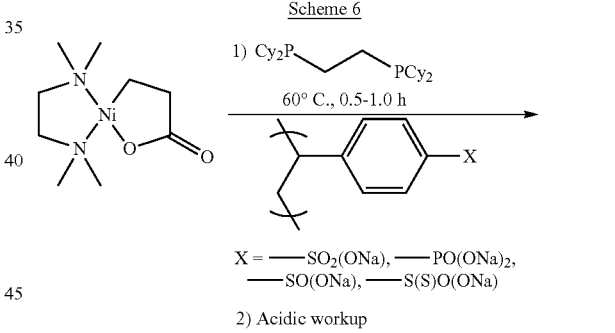

X = ––SO$_2$(ONa), ––PO(ONa)$_2$,
––SO(ONa), ––S(S)O(ONa)

2) Acidic workup

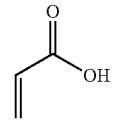

TABLE 2

Exemplary sulfur and phosphorus oxoacid anion-substituted polymers and copolymers

| Example | Polyaromatic Resin | Solvent |
|---|---|---|
| 21 | Sodium poly(4-vinylbenzenesulfonate) | Toluene, THF |
| 22 | Sodium poly(4-vinylbenzenephosphonate) | Toluene, THF |
| 23 | Sodium poly(4-vinylbenzenesulfinate) | Toluene, THF |
| 24 | Sodium poly(4-vinylbenzenethiosulfonate) | Toluene, THF |
| 25 | Sodium poly(4-vinylbenzenethiosulfinate) | Toluene, THF |
| 26 | Sodium poly(4-vinylbenzenesulfonate-co-methyl(meth)acrylate) | Toluene, THF |
| 27 | Sodium poly(4-vinylbenzenephosphonate-co-methyl(meth)acrylate) | Toluene, THF |

TABLE 2-continued

Exemplary sulfur and phosphorus oxoacid anion-substituted polymers and copolymers

| Example | Polyaromatic Resin | Solvent |
|---|---|---|
| 28 | Sodium poly(4-vinylbenzenesulfinate-co-methyl(meth)acrylate) | Toluene, THF |
| 29 | Sodium poly(4-vinylbenzenethiosulfonate-co-methyl(meth)acrylate) | Toluene, THF |
| 30 | Sodium poly(4-vinylbenzenethiosulfinate-co-methyl(meth)acrylate) | Toluene, THF |
| 31 | Sodium poly(4-vinylbenzenesulfonate-co-divinylbenzene) | Toluene, THF |
| 32 | Sodium poly(4-vinylbenzenephosphonate-co-divinylbenzene) | Toluene, THF |
| 33 | Sodium poly(4-vinylbenzenesulfinate-co-divinylbenzene) | Toluene, THF |
| 34 | Sodium poly(4-vinylbenzenethiosulfonate-co-divinylbenzene) | Toluene, THF |
| 35 | Sodium poly(4-vinylbenzenethiosulfinate-co-divinylbenzene) | Toluene, THF |
| 36 | AMBERLITE ® IR120 Na | Toluene, THF |
| 37 | AMBERLYST ® | Toluene, THF |

Additional resin types that can be employed according to the reaction Scheme 6 and this disclosure are illustrated in the following reaction Scheme 7, and reaction parameters such as disclosed in the table above can be utilized in this reaction scheme as well.

Scheme 7

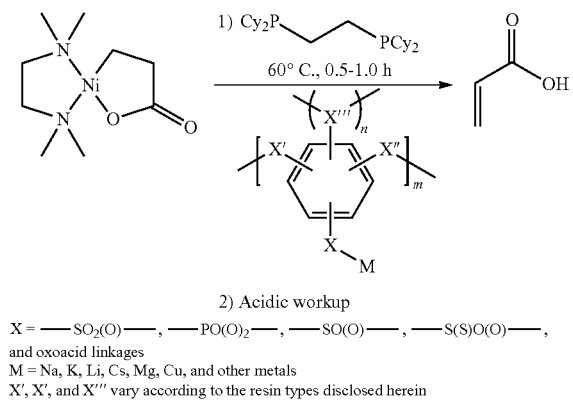

X = —SO$_2$(O)—, —PO(O)$_2$—, —SO(O)—, —S(S)O(O)—, and oxoacid linkages
M = Na, K, Li, Cs, Mg, Cu, and other metals
X', X', and X''' vary according to the resin types disclosed herein Examples 38-39

Commercial Sulfur Oxoacid Anion-Substituted Resins as Stoichiometric Co-Catalysts in Olefin/Carbon Dioxide Conversion to α,β-Unsaturated Carboxylates and their Regeneration Because various sulfur oxoacid anion-substituted polyaromatic resin or the phosphorus oxoacid anion-substituted polyaromatic resins were found to be suitable promoters and sources of cations in the conversion of olefin and carbon dioxide-derived nickelalactone intermediates, an evaluation of their crosslinked analogues was undertaken. It was believed that these crosslinked polyaromatic resins would be sufficiently insoluble in many commercial diluents and be applicable as a polymeric promoters and cation sources in a fixed bed and/or column reactor setting. This method further allows for the potential regeneration of the spent solid co-catalyst in both aqueous (for example, sodium hydroxide in water) and/or organic media (for example, sodium alkoxide in toluene) and using sodium chloride as a sodium source.

In these examples, commercially available sodium form of AMBERLITE®, a crosslinked polystyrene sulfonate resin, was used in the coupling reaction of CO$_2$ and ethylene, and was found to be effective as a heterogeneous solid activator (co-catalyst) in the process. The AMBERLITE® used is described as a styrene divinylbenzene sulfonated. Scheme 8 illustrates the conversion reaction of an olefin and carbon dioxide-derived nickelalactone intermediate that was undertaken to evaluate some crosslinked polyaromatic e analogues. Reaction conditions for Scheme 8 are: 0.10 mmol [Ni], 0.11 mmol diphosphine ligand, 500 mL of toluene, 1.0 g of sodium-treated, crosslinked polyaromatic resin (solid activator). The reactor was equilibrated to 150 psi of ethylene followed by 300 psi of carbon dioxide prior to heating. The yield reported in Table 3 was determined by $^1$H NMR spectroscopy in a D$_2$O/(CD$_3$)$_2$CO mixture relative to a sorbic acid standard.

Scheme 8

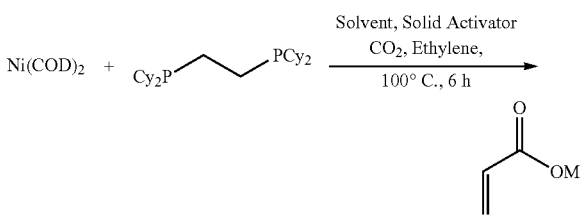

TABLE 3

Coupling reactions using commercial resins

| Example | Solid Activator | Resin Type | Acrylate Yield (%) |
|---|---|---|---|
| 38 | AMBERLITE ® 120 Na+ | Sulfonated, dried [A] | 6.7 |
| 39 | AMBERLITE ® 120 Na+ | Sulfonated, not dried [B] | Not detected |

[A] Resin was dried in the reactor under a nitrogen stream at 100° C. prior to the reaction.
[B] Resin was used without further treatment.

Example 40

Polymeric Stationary Phases for Catalytic Acrylate Formation

The present disclosure also provides for using polymeric stationary phases comprising the sulfur oxoacid anion-substituted polyaromatic resin or the phosphorus oxoacid anion-substituted polyaromatic resins, such as functionalized polystyrenes or phenol-formaldehyde type resins, in a column or other suitable solid state configuration, in which formation of the acrylate from a metalalactone (such as a nickelalactone) in a mobile phase can be effected.

FIG. 1 illustrates one way in which a polymeric stationary phase catalyst column can be configured, in which the coupling reaction and elution of the metal acrylate from the column can be carried out. As shown, a sulfonated, a phosphonated, a sulfinated, a thiosulfonated, or a thiosulfinated polystyrene or styrene-divinylbenzene copolymer can be used according to FIG. 1. This method can provide both easier separation of acrylate from other materials and ease of regeneration of the polymeric support materials to its salt form, such as sodium poly(4-vinylphenoxide).

Example 41

Crosslinked Polyaromatic Resin Co-Catalysts in Olefin/Carbon Dioxide Conversion to α,β-Unsaturated Carboxylates, Using Co-Monomers In this example, co-monomer phenol compounds are used together with formaldehyde to prepare the crosslinked polyaromatic resins for use as described according to the disclosure. The resin was prepared using the co-monomer combination of resorcinol (m-dihydroxybenzene) and 2-fluorophenol monomer with formaldehyde, and the resulting resin was sodium-treated (NaOH, dissolved in water or alcohol) to generate the anionic polyelectrolyte, according to equation (4).

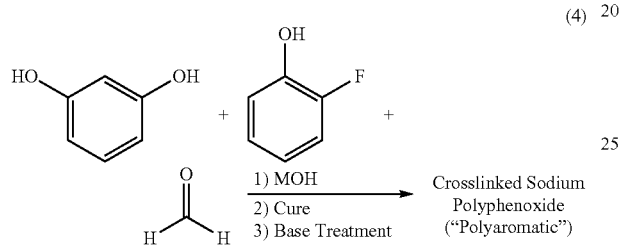

(4)

Once prepared, the resulting polyaromatic resin can be functionalized, for example, with sulfonic acid groups, phosphonic acid groups, sulfinic acid groups, thiosulfonic acid groups, and/or thiosulfinic acid groups and treated with sodium hydroxide or another base to form the corresponding s a sulfonated, a phosphonated, a sulfinated, a thiosulfonated, or a thiosulfinated materials, which can promote nickelalactone scission.

In an aspect, such crosslinked resins can be converted into a porous carbonaceous material upon the pyrolysis of the phenol formaldehyde resin. These pyrolyzed materials, in turn, can be functionalized by various treatments to provide sulfur oxoacid anion-substituted polyaromatic resin or the phosphorus oxoacid anion-substituted polyaromatic resin materials. For example, pyrolyzed materials may be sulfonated by sulfuric acid treatment. Similarly, the pyrolyzed materials may be sulfinated by $SO_2$ treatment, sulfonic acid treatment, or sulfinic acid treatment of the porous carbonaceous material derived from the pyrolysis. The thiosulfonated polyaromatic resin can generated by, for example, thiosulfonic acid treatment of this porous carbonaceous material. The phosphonated polyaromatic resin also can be formed by aromatic substitution with a chlorinated phosphine, followed by alcoholic or aqueous workup, of a crosslinked polystyrene or a porous carbonaceous material derived from the pyrolysis of a phenol formaldehyde resin.

The invention is described above with reference to numerous aspects and embodiments, and specific examples. Many variations will suggest themselves to those skilled in the art in light of the above detailed description. All such obvious variations are within the full intended scope of the appended claims. Other aspects of the invention can include, but are not limited to, the following aspects. Many aspects are described as "comprising" certain components or steps, but alternatively, can "consist essentially of" or "consist of" those components or steps unless specifically stated otherwise.

Aspect 1. A process for forming an α,β-unsaturated carboxylic acid or salt thereof, the process comprising
  a) contacting
    1) a metalalactone compound;
    2) a diluent; and
    3) a sulfur oxoacid anion-substituted polyaromatic resin or a phosphorus oxoacid anion-substituted polyaromatic resin; wherein the polyaromatic resin further comprises associated metal cations to provide a reaction mixture; and
  b) applying reaction conditions to the reaction mixture suitable to form the α,β-unsaturated carboxylic acid or the salt thereof.

Aspect 2. A process for forming an α,β-unsaturated carboxylic acid or a salt thereof, the process comprising:
  a) contacting
    1) a metalalactone compound;
    2) a diluent; and
    3) a sulfur oxoacid anion-substituted polyaromatic resin or a phosphorus oxoacid anion-substituted polyaromatic resin; wherein the polyaromatic resin further comprises associated metal cations, to provide a reaction mixture comprising an adduct of the metalalactone and sulfur oxoacid anion-substituted polyaromatic resin or a phosphorus oxoacid anion-substituted polyaromatic resin; and
  b) applying reaction conditions to the reaction mixture suitable to induce a metalalactone elimination reaction to produce the α,β-unsaturated carboxylic acid or the salt thereof.

Aspect 3. A process for forming an α,β-unsaturated carboxylic acid or a salt thereof, the process comprising:
  a) contacting in any order
    1) a transition metal precursor compound comprising at least one first ligand;
    2) optionally, at least one second ligand;
    3) an olefin;
    4) carbon dioxide ($CO_2$);
    5) a diluent; and
    6) a sulfur oxoacid anion-substituted polyaromatic resin or a phosphorus oxoacid anion-substituted polyaromatic resin; wherein the polyaromatic resin further comprises associated metal cations to provide a reaction mixture; and
  b) applying reaction conditions to the reaction mixture suitable to form the α,β-unsaturated carboxylic acid or the salt thereof.

Aspect 4. The process according to any one of Aspects 1-3, wherein the sulfur oxoacid anion-substituted polyaromatic resin or the phosphorus oxoacid anion-substituted polyaromatic resin comprises a sulfonated polyaromatic resin, a phosphonated polyaromatic resin, a sulfinated polyaromatic resin, a thiosulfonated polyaromatic resin, or a thiosulfinated polyaromatic resin.

Aspect 5. The process according to any one of Aspects 1-3, wherein the sulfur oxoacid anion-substituted polyaromatic resin or the phosphorus oxoacid anion-substituted polyaromatic resin comprises a sulfonated, a phosphonated, a sulfinated, a thiosulfonated, or a thiosulfinated styrene polymer or copolymer.

Aspect 6. The process according to any one of Aspects 1-3, wherein the sulfur oxoacid anion-substituted polyaromatic resin or the phosphorus oxoacid anion-substituted polyaromatic resin comprises a sulfonated, a phosphonated, a sulfinated, a thiosulfonated, or a thiosulfinated styrene-divinylarene copolymer.

Aspect 7. The process according to any one of Aspects 1-3, wherein the sulfur oxoacid anion-substituted polyaromatic resin or the phosphorus oxoacid anion-substituted polyaromatic resin comprises a sulfonated, a phosphonated, a sulfinated, a thiosulfonated, or a thiosulfinated styrene-divinylbenzene copolymer.

Aspect 8. The process according to any one of Aspects 1-3, wherein the sulfur oxoacid anion-substituted polyaromatic resin or the phosphorus oxoacid anion-substituted polyaromatic resin comprises a macroreticular sulfonated, a macroreticular phosphonated, a macroreticular sulfinated, a macroreticular thiosulfonated, or a macroreticular thiosulfinated styrene-divinylbenzene copolymer.

Aspect 9. The process according to any one of Aspects 1-7, wherein the sulfur oxoacid anion-substituted polyaromatic resin or the phosphorus oxoacid anion-substituted polyaromatic resin has an average particle size from about 0.1 mm to about 1.0 mm.

Aspect 10. The process according to any one of Aspects 1-7, wherein the sulfur oxoacid anion-substituted polyaromatic resin or the phosphorus oxoacid anion-substituted polyaromatic resin has an average particle size from about 0.50 mm to about 0.80 mm.

Aspect 11. The process according to any one of Aspects 1-9, wherein the sulfur oxoacid anion-substituted polyaromatic resin or the phosphorus oxoacid anion-substituted polyaromatic resin is insoluble in the diluent or the reaction mixture.

Aspect 12. The process according to any one of Aspects 1-9, wherein the sulfur oxoacid anion-substituted polyaromatic resin or the phosphorus oxoacid anion-substituted polyaromatic resin is soluble in the diluent or the reaction mixture.

Aspect 13. The process according to any one of Aspects 1 or 4-11, wherein the reaction mixture comprises an adduct of the metalalactone and the sulfur oxoacid anion-substituted polyaromatic resin or the phosphorus oxoacid anion-substituted polyaromatic resin.

Aspect 14. The process according to any one of Aspects 1-12, wherein the associated metal cations are selected from a Group 1, 2, 12 or 13 metal.

Aspect 15. The process according to any one of Aspects 1-13, wherein the sulfur oxoacid anion-substituted polyaromatic resin or the phosphorus oxoacid anion-substituted polyaromatic resin is macroporous, having an average pore diameter greater than about 50 nm.

Aspect 16. The process according to any one of Aspects 1-13, wherein the sulfur oxoacid anion-substituted polyaromatic resin or the phosphorus oxoacid anion-substituted polyaromatic resin has an average pore diameter from about 50 nm to about 250 nm.

Aspect 17. The process according to any one of Aspects 1-15, wherein the associated metal cations comprise any suitable Lewis acidic metal cation or any Lewis acidic metal cation disclosed herein.

Aspect 18. The process according to any one of Aspects 1-15, wherein the associated metal cations are an alkali metal, an alkaline earth metal, or a combination thereof.

Aspect 19. The process according to any one of Aspects 1-15, wherein the associated metal cations are lithium, sodium, potassium, rubidium, cesium, magnesium, calcium, strontium, barium, zinc, aluminum, or gallium.

Aspect 20. The process according to any one of Aspects 1-15, wherein the associated metal cations are sodium or potassium.

Aspect 21. The process according to any one of Aspects 1-15, wherein the wherein the sulfur oxoacid anion-substituted polyaromatic resin is an AMBERLITE® or AMBERLYST® resin.

Aspect 22. The process according to any one of Aspects 1-19, wherein the sulfonated polyaromatic resin is generated by sulfuric acid treatment of a crosslinked polystyrene or a porous carbonaceous material derived from the pyrolysis of a phenol formaldehyde resin.

Aspect 23. The process according to any one of Aspects 1-19, wherein the sulfur oxoacid anion-substituted polyaromatic resin is generated by $SO_2$ treatment (e.g. $SO_2$(aq)), sulfonic acid treatment, sulfinic acid treatment, thiosulfonic acid treatment, or thiosulfinic acid treatment of a crosslinked polystyrene or a porous carbonaceous material derived from the pyrolysis of a phenol formaldehyde resin.

Aspect 24. The process according to any one of Aspects 1-19, wherein the phosphonated polyaromatic resin is generated by aromatic substitution with a chlorinated phosphine, followed by alcoholic or aqueous workup, of a crosslinked polystyrene or a porous carbonaceous material derived from the pyrolysis of a phenol formaldehyde resin.

Aspect 25. The process according to any one of Aspects 1-22, wherein the diluent comprises any suitable non-protic solvent, or any non-protic solvent disclosed herein.

Aspect 26. The process according to any one of Aspects 1-22, wherein the diluent comprises any suitable weakly coordinating or non-coordinating solvent, or any weakly coordinating or non-coordinating solvent disclosed herein.

Aspect 27. The process according to any one of Aspects 1-22, wherein the diluent comprises any suitable aromatic hydrocarbon solvent, or any aromatic hydrocarbon solvent disclosed herein, e.g., benzene, xylene, toluene, etc.

Aspect 28. The process according to any one of Aspects 1-22, wherein the diluent comprises any suitable ether solvent, or any ether solvent disclosed herein, e.g., THF, dimethyl ether, diethyl ether, dibutyl ether, etc.

Aspect 29. The process according to any one of Aspects 1-22, wherein the diluent comprises any suitable carbonyl-containing solvent, or any carbonyl-containing solvent disclosed herein, e.g., ketones, esters, amides, etc. (e.g., acetone, ethyl acetate, N,N-dimethylformamide, etc.).

Aspect 30. The process according to any one of Aspects 1-22, wherein the diluent comprises any suitable halogenated aromatic hydrocarbon solvent, or any halogenated aromatic hydrocarbon solvent disclosed herein, e.g., chlorobenzene, dichlorobenzene, etc.

Aspect 31. The process according to any one of Aspects 1-22, wherein the diluent comprises THF, 2,5-Me$_2$THF, methanol, acetone, toluene, chlorobenzene, pyridine, or a combination thereof.

Aspect 32. The process according to any one of Aspects 1-29, wherein the diluent comprises carbon dioxide.

Aspect 33. The process according to any one of Aspects 1-30, wherein at least a portion of the diluent comprises the α,β-unsaturated carboxylic acid or the salt thereof, formed in the process.

Aspect 34. The process according to any one of Aspects 1-31, wherein the contacting step further comprises contacting an additive selected from an acid, a base, or a reductant.

Aspect 35. The process according to any one of Aspects 3-31, wherein the contacting step comprises contacting the transition metal precursor compound comprising at least one first ligand with the at least one second ligand.

Aspect 36. The process according to any one of Aspects 3-31, wherein the contacting step comprises contacting 1) the transition metal precursor compound comprising at least one first ligand with 2) the at least one second ligand to form a pre-contacted mixture, followed by contacting the pre-contacted mixture with the remaining components 3)-6) in any order to provide the reaction mixture.

Aspect 37. The process according to any one of Aspects 1-2 or 4-31, wherein the contacting step comprises contacting the metalalactone, the diluent, and the sulfur oxoacid anion-substituted polyaromatic resin or the phosphorus oxoacid anion-substituted polyaromatic resin in any order.

Aspect 38. The process according to any one of Aspects 1-2 or 4-31, wherein the contacting step comprises contacting the metalalactone and the diluent to form a first mixture, followed by contacting the first mixture with the sulfur oxoacid anion-substituted polyaromatic resin or the phosphorus oxoacid anion-substituted polyaromatic resin to form the reaction mixture.

Aspect 39. The process according to any one of Aspects 1-2 or 4-31, wherein the contacting step comprises contacting the diluent and the sulfur oxoacid anion-substituted polyaromatic resin or the phosphorus oxoacid anion-substituted polyaromatic resin to form a first mixture, followed by contacting the first mixture with the metalalactone to form the reaction mixture.

Aspect 40. The process according to any one of Aspects 1-31, wherein the reaction conditions suitable to form the α,β-unsaturated carboxylic acid or the salt thereof comprise contacting the reaction mixture with any suitable acid, or any acid disclosed herein, e.g., HCl, acetic acid, etc.

Aspect 41. The process according to any one of Aspects 1-31, wherein the reaction conditions suitable to form the α,β-unsaturated carboxylic acid or the salt thereof comprise contacting the reaction mixture with any suitable solvent, or any solvent disclosed herein, e.g., carbonyl-containing solvents such as ketones, esters, amides, etc. (e.g., acetone, ethyl acetate, N,N-dimethylformamide), alcohols, water, etc.

Aspect 42. The process according to any one of Aspects 1-39, wherein the reaction conditions suitable to form the α,β-unsaturated carboxylic acid or the salt thereof comprise heating the reaction mixture to any suitable temperature, or a temperature in any range disclosed herein, e.g., from 50 to 1000° C., from 100 to 800° C., from 150 to 600° C., from 250 to 550° C., etc.

Aspect 43. The process according to any one of Aspects 1-40, wherein the molar yield of the α,β-unsaturated carboxylic acid, or the salt thereof, based on the metalalactone (in those preceding Aspects comprising a metalalactone) or based on the transition metal precursor compound (in those preceding Aspects comprising a transition metal precursor compound) is in any range disclosed herein, e.g., at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%, etc.

Aspect 44. The process according to any one of Aspects 1-41, wherein the contacting step and/or the applying step is/are conducted at any suitable pressure or at any pressure disclosed herein, e.g., from 5 psig (34 KPa) to 10,000 psig (68,948 KPa), from 45 psig (310 KPa) to 1000 psig (6,895 KPa), etc.

Aspect 45. The process according to any one of Aspects 1-42, wherein the contacting step and/or the applying step is/are conducted at any suitable temperature or at any temperature disclosed herein, e.g., from 0° C. to 250° C., from 0° C. to 95° C., from 15° C. to 70° C., etc.

Aspect 46. The process according to any one of the Aspects 1-43, wherein the contacting step and/or the applying step is conducted at any suitable weight hourly space velocity (WHSV) or any WHSV disclosed herein, e.g., from 0.05 to 50 hr$^{-1}$, from 1 to 25 hr$^{-1}$, from 1 to 5 hr$^{-1}$, etc., based on the amount of the sulfur oxoacid anion-substituted polyaromatic resin or the phosphorus oxoacid anion-substituted polyaromatic resin.

Aspect 47. The process according to any one of Aspects 1-44, wherein the process further comprises a step of isolating the α,β-unsaturated carboxylic acid, or the salt thereof, e.g., using any suitable separation/purification procedure or any separation/purification procedure disclosed herein, e.g., evaporation, distillation, chromatography, etc.

Aspect 48. The process according to any one of Aspects 1-45, wherein the sulfur oxoacid anion-substituted polyaromatic resin or the phosphorus oxoacid anion-substituted polyaromatic resin of the contacting step a) is arranged as a fixed bed, a bubbling bed, a moving bed, or a stirred bed.

Aspect 49. The process according to any one of Aspects 1-45, wherein the sulfur oxoacid anion-substituted polyaromatic resin or the phosphorus oxoacid anion-substituted polyaromatic resin of the contacting step a) is formed into a bead, is supported onto an inert inorganic support, is supported onto an inert organic support, or is used in the absence of a support.

Aspect 50. The process according to any one of Aspects 1-45, wherein the contacting step a) is carried out by mixing/stirring the sulfonated polyaromatic resin or the phosphonated polyaromatic resin in the diluent.

Aspect 51. The process according to any one of Aspects 1-48, wherein the α,β-unsaturated carboxylic acid or the salt thereof comprises any suitable α,β-unsaturated carboxylic acid, or any α,β-unsaturated carboxylic acid disclosed herein, or the salt thereof, e.g., acrylic acid, methacrylic acid, 2-ethylacrylic acid, cinnamic acid, sodium acrylate, potassium acrylate, magnesium acrylate, sodium (meth) acrylate, etc.

Aspect 52. The process according to any one of Aspects 3-49, further comprising a step of contacting a transition metal precursor compound comprising at least one first ligand, an olefin, and carbon dioxide ($CO_2$) to form the metalalactone compound.

Aspect 53. The process according to any one of Aspects 3-49, further comprising a step of contacting a transition metal precursor compound comprising at least one first ligand, at least one second ligand, an olefin, and carbon dioxide ($CO_2$) to form the metalalactone compound.

Aspect 54. The process according to Aspect 51, wherein the metalalactone compound comprises the at least one first ligand, the at least one second ligand, or a combination thereof.

Aspect 55. The process according to any one of Aspects 1-2 or 4-52, wherein the metalalactone compound comprises the at least one second ligand.

Aspect 56. The process according to any one of Aspects 3-53, wherein the olefin comprises any suitable olefin or any olefin disclosed herein, e.g. ethylene, propylene, butene (e.g., 1-butene), pentene, hexene (e.g., 1-hexene), heptane, octene (e.g., 1-octene), styrene, etc.

Aspect 57. The process according to any one of Aspects 3-54, wherein the olefin is ethylene, and the step of contacting a transition metal precursor compound with an olefin and carbon dioxide ($CO_2$) is conducted using any suitable pressure of ethylene, or any pressure of ethylene disclosed herein, e.g., from 10 psig (69 KPa) to 1,000 psig (6895 KPa), from 25 psig (172 KPa) to 500 psig (3,447 KPa), or from 50 psig (345 KPa) to 300 psig (2,068 KPa), etc.

Aspect 58. The process according to any one of Aspects 3-55, wherein the olefin is ethylene, and the step of contacting a transition metal precursor compound with an olefin and carbon dioxide ($CO_2$) is conducted using a constant addition of the olefin and carbon dioxide to provide the reaction mixture.

Aspect 59. The process according to Aspect 56, wherein the ethylene and carbon dioxide ($CO_2$) are constantly added in an ethylene:$CO_2$ molar ratio of from 3:1 to 1:3, to provide the reaction mixture.

Aspect 60. The process according to any one of Aspects 3-57, wherein the step of contacting a transition metal precursor compound with the olefin and carbon dioxide ($CO_2$) is conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), etc.

Aspect 61. The process according to any one of Aspects 1-58, further comprising a step of monitoring the concentration of at least one reaction mixture component, at least one elimination reaction product, or a combination thereof.

Aspect 62. The process according to any one of Aspects 1-59, wherein the metal of the metalalactone or the metal of the transition metal precursor compound is a Group 8-11 transition metal.

Aspect 63. The process according to any one of Aspects 1-59, wherein the metal of the metalalactone or the metal of the transition metal precursor compound is Cr, Fe, Co, Ni, Cu, Mo, Ru, Rh, Pd, W, Ag, Ir, Pt, or Au.

Aspect 64. The process according to any one of Aspects 1-59, wherein the metal of the metalalactone or the metal of the transition metal precursor compound is Ni, Fe, or Rh.

Aspect 65. The process according to any one of Aspects 1-59, wherein the metal of the metalalactone or the metal of the transition metal precursor compound is Ni.

Aspect 66. The process according to any one of Aspects 1-59, wherein the metalalactone is a nickelalactone, e.g., any suitable nickelalactone or any nickelalactone disclosed herein, or wherein the metal of the transition metal precursor compound is Ni.

Aspect 67. The process according to any one of Aspects 1-64, wherein any ligand of the metalalactone compound, the first ligand, or the second ligand is any suitable neutral electron donor group and/or Lewis base, or any neutral electron donor group and/or Lewis base disclosed herein.

Aspect 68. The process according to any one of Aspects 1-64, wherein any ligand of the metalalactone compound, the first ligand, or the second ligand is a bidentate ligand.

Aspect 69. The process according to any one of Aspects 1-64, wherein any ligand of the metalalactone compound, the first ligand, or the second ligand comprises at least one of a nitrogen, phosphorus, sulfur, or oxygen heteroatom.

Aspect 70. The process according to any one of Aspects 1-64, wherein any ligand of the metalalactone compound, the first ligand, or the second ligand comprises or is selected from a diphosphine ligand, a diamine ligand, a diene ligand, a diether ligand, or dithioether ligand.

Aspect 71. The process according to any one of Aspects 1-64, wherein any ligand of the metalalactone compound, the first ligand, or the second ligand comprises or is selected from a) an asymmetric ligand (comprising different donor atoms) such as 2-pyridylphosphine or b) an N-heterocyclic carbene (NHC) ligand.

Aspect 72. The process according to any one of Aspects 1-69, further comprising a step of regenerating the sulfur oxoacid anion-substituted polyaromatic resin or the phosphorus oxoacid anion-substituted polyaromatic resin, by contacting a by-product acid form of the sulfur oxoacid anion-substituted polyaromatic resin or the phosphorus oxoacid anion-substituted polyaromatic resin that is generated from the process with a metal-containing base or with a metal-containing salt.

Aspect 73. The process according to Aspect 72, wherein: the metal-containing base comprises any suitable base, or any base disclosed herein, e.g., carbonates (e.g., $Na_2CO_3$, $Cs_2CO_3$, $MgCO_3$), hydroxides (e.g., $Mg(OH)_2$, NaOH), alkoxides (e.g., $Al(O^iPr)_3$, $Na(O^tBu)$, $Mg(OEt)_2$), aryloxides (e.g. $Na(OC_6H_5)$, sodium phenoxide), sulfates (e.g. $Na_2SO_4$, $K_2SO_4$, $CaSO_4$, $MgSO_4$), etc.; and the metal-containing salt comprises sodium chloride, potassium chloride, etc.

Aspect 74. The process according to any one of Aspects 1-69, further comprising a step of regenerating the sulfur oxoacid anion-substituted polyaromatic resin or the phosphorus oxoacid anion-substituted polyaromatic resin by contacting a by-product resin that is generated from the process with an aqueous sodium ion ($Na^+$) source.

Aspect 75. The process according to any one of Aspects 1-69, further comprising a step of regenerating the sulfur oxoacid anion-substituted polyaromatic resin or the phosphorus oxoacid anion-substituted polyaromatic resin by contacting a by-product resin that is generated from the process with aqueous sodium halide (brine).

Aspect 76. The process according to any one of Aspects 1-69, further comprising a step of regenerating the sulfur oxoacid anion-substituted polyaromatic resin or the phosphorus oxoacid anion-substituted polyaromatic resin by contacting a by-product resin that is generated from the process with an aqueous acid and an aqueous brine.

Aspect 77. The process according to Aspect 74, wherein the by-product resin is contacted with aqueous acid followed by aqueous brine, or wherein the by-product resin is contacted with aqueous acid and aqueous brine at the same time.

Aspect 78. The process according to Aspect 74, wherein the by-product resin is contacted with aqueous acid, followed by an aqueous wash step, followed by contacting with aqueous brine.

Aspect 79. The process according to any one of Aspects 1-69, further comprising a step of regenerating the sulfur oxoacid anion-substituted polyaromatic resin or the phosphorus oxoacid anion-substituted polyaromatic resin by contacting a by-product resin that is generated from the process with aqueous solution of about 5 wt % to about 15 wt % sodium chloride.

Aspect 80. The process according to any one of Aspects 70-77, further comprising a step of washing the regenerated sulfur oxoacid anion-substituted polyaromatic resin or the regenerated phosphorus oxoacid anion-substituted polyaromatic resin with a solvent or the diluent following the step of regenerating the sulfur oxoacid anion-substituted polyaromatic resin or the phosphorus oxoacid anion-substituted polyaromatic resin.

Aspect 81. The process according to any one of Aspects 70-77, wherein the step of regenerating the sulfur oxoacid anion-substituted polyaromatic resin or the phosphorus oxoacid anion-substituted polyaromatic resin is carried out in the absence of an alkoxide, an aryloxide, an amide, an alkylamide, an arylamide, an amine, a hydride, a phosphazene, and/or substituted analogs thereof.

Aspect 82. The process according to any one of Aspects 70-77, wherein the step of regenerating the sulfur oxoacid anion-substituted polyaromatic resin or the phosphorus oxoacid anion-substituted polyaromatic resin is carried out in the absence of an alkoxide, an aryloxide, a hydride, and/or a phosphazene.

Aspect 83. The process according to any one of Aspects 70-77, wherein the step of regenerating the sulfur oxoacid anion-substituted polyaromatic resin or the phosphorus oxoacid anion-substituted polyaromatic resin is carried out in the absence of an aryloxide or a metal hydride.

Aspect 84. The process according to any one of Aspects 70-77, wherein the step of regenerating the sulfur oxoacid anion-substituted polyaromatic resin or the phosphorus oxoacid anion-substituted polyaromatic resin is carried out in the absence of a non-nucleophilic base.

Aspect 85. The process according to any one of Aspects 70-77, wherein the sulfur oxoacid anion-substituted polyaromatic resin or the phosphorus oxoacid anion-substituted polyaromatic resin is unsupported.

Aspect 86. The process according to any one of Aspects 70-77, wherein the sulfur oxoacid anion-substituted polyaromatic resin or the phosphorus oxoacid anion-substituted polyaromatic resin is supported.

Aspect 87. The process according to any one of Aspects 1-84, wherein the metalalactone, the metalalactone ligand (that is, any ligand of the metalalactone compound other than the metalalactone moiety), the transition metal precursor compound, the first ligand, the second ligand, the sulfur oxoacid anion-substituted polyaromatic resin or the phosphorus oxoacid anion-substituted polyaromatic resin, or the metal cation is any suitable metalalactone, additional ligand of the metalalactone compound, transition metal precursor compound, first ligand, second ligand, sulfonated polyaromatic resin or the phosphonated polyaromatic resin, or metal cation or is any metalalactone, metalalactone ligand, sition metal precursor compound, first ligand, second ligand, sulfur oxoacid anion-substituted polyaromatic resin or phosphorus oxoacid anion-substituted polyaromatic resin, or metal cation disclosed herein.

Aspect 88. A process for forming an $\alpha,\beta$-unsaturated carboxylic acid or salt thereof, the process comprising:
(1) contacting
  (a) a metalalactone comprising a Group 8-10 metal and at least one ligand;
  (b) a diluent; and
  (c) a sulfur oxoacid anion-substituted polyaromatic resin or a phosphorus oxoacid anion-substituted polyaromatic resin; wherein the polyaromatic resin further comprises associated metal cations to provide a reaction mixture; and
(2) applying reaction conditions to the reaction mixture suitable to induce a metalalactone elimination reaction to form the $\alpha,\beta$-unsaturated carboxylic acid or the salt thereof.

Aspect 89. A process for forming an $\alpha,\beta$-unsaturated carboxylic acid or a salt thereof, the process comprising:
(1) contacting in any order
  (a) a group 8-11 transition metal precursor;
  (b) an olefin;
  (c) carbon dioxide ($CO_2$);
  (d) a diluent; and
  (e) a sulfur oxoacid anion-substituted polyaromatic resin or a phosphorus oxoacid anion-substituted polyaromatic resin; wherein the polyaromatic resin further comprises associated metal cations to provide a reaction mixture; and
(2) applying reaction conditions to the reaction mixture suitable to produce the $\alpha,\beta$-unsaturated carboxylic acid or the salt thereof.

Aspect 90. A process for forming an $\alpha,\beta$-unsaturated carboxylic acid or a salt thereof, the process comprising:
(1) contacting in any order
  (a) a group 8-11 transition metal catalyst;
  (b) an olefin;
  (c) carbon dioxide ($CO_2$);
  (d) a diluent; and
  (e) a sulfur oxoacid anion-substituted polyaromatic resin or a phosphorus oxoacid anion-substituted polyaromatic resin; wherein the polyaromatic resin further comprises associated metal cations to provide a reaction mixture; and
(2) contacting the reaction mixture with a metal-containing base selected from an alkali metal or an alkaline earth metal oxide, hydroxide, alkoxide, aryloxide, amide, alkyl amide, arylamide, or carbonate to produce an $\alpha,\beta$-unsaturated carboxylic acid salt;
wherein the contacting step is carried out in the absence of a non-nucleophilic base.

The invention claimed is:
1. A catalyst system for forming an $\alpha,\beta$-unsaturated carboxylic acid or a salt thereof, the catalyst system comprising:
  a) a transition metal precursor comprising a Group 8-10 transition metal and at least one first ligand;
  b) optionally, at least one second ligand;
  c) an olefin;
  d) carbon dioxide ($CO_2$);
  e) a diluent; and
  f) an oxoacid anion-substituted polyaromatic resin comprising a sulfonated polyaromatic resin, a phosphonated polyaromatic resin, a sulfinated polyaromatic resin, a thiosulfonated, or a thiosulfinated polyaromatic resin, and further comprising associated metal cations.

2. The catalyst system according to claim 1, wherein the catalyst system further comprises a Group 8-10 transition metal metalalactone compound or an adduct of a Group 8-10 transition metal metalalactone compound and the oxoacid anion-substituted polyaromatic resin.

3. The catalyst system according to claim 1, wherein the oxoacid anion-substituted polyaromatic resin has a) an average particle size from about 0.1 mm to about 1.0 mm, b) an average pore diameter from about 50 nm to about 250 nm, or c) both an average particle size from about 0.1 mm to about 1.0 mm and an average pore diameter from about 50 nm to about 250 nm.

4. The catalyst system according to claim 1, wherein:
the oxoacid anion-substituted polyaromatic resin is formed into a bead, supported onto an inert inorganic support, supported onto an inert organic support, or used in the absence of a support; and
the oxoacid anion-substituted polyaromatic resin is arranged as a fixed bed, a bubbling bed, a moving bed, or a stirred bed.

5. The catalyst system according to claim 1, wherein:
the first ligand and the second ligand are selected independently from a diphosphine ligand, a diamine ligand, a diene ligand, a diether ligand, or dithioether ligand; and
the associated metal cations are selected from a Group 1, 2, 12, or 13 metal.

6. The catalyst system according to claim 1, wherein the olefin comprises ethylene, propylene, butene, pentene, hexene, heptane, octene, or styrene.

7. The catalyst system according to claim 1, wherein the α,β-unsaturated carboxylic acid or the salt thereof is acrylic acid, methacrylic acid, 2-ethylacrylic acid, cinnamic acid, or a salt thereof.

8. A process for forming an α,β-unsaturated carboxylic acid or a salt thereof, the process comprising:
a) contacting in any order
1) A transition metal precursor comprising a Group 8-10 transition metal and at least one first ligand;
2) Optionally, at least one second ligand;
3) An olefin;
4) Carbon dioxide ($CO_2$);
5) A diluent; and
6) an oxoacid anion-substituted polyaromatic resin comprising a sulfonated polyaromatic resin, a phosphonated polyaromatic resin, a sulfinated polyaromatic resin, a thiosulfonated resin, or a thiosulfinated polyaromatic resin, further comprising associated metal cations, to provide a reaction mixture; and
b) applying reaction conditions to the reaction mixture suitable to form the α,β-unsaturated carboxylic acid or the salt thereof.

9. The process according to claim 8, wherein the reaction mixture comprises a Group 8-10 transition metal metalalactone compound or an adduct of a Group 8-10 transition metal metalalactone compound and the oxoacid anion-substituted polyaromatic resin and associated metal cations, and wherein the reaction conditions suitable to form the α,β-unsaturated carboxylic acid or the salt thereof induces a metalalactone elimination reaction to produce the α,β-unsaturated carboxylic acid or the salt thereof.

10. The process according to claim 8, wherein the oxoacid anion-substituted polyaromatic resin has a) an average particle size from about 0.1 mm to about 1.0 mm, b) an average pore diameter from about 50 nm to about 250 nm, or c) both an average particle size from about 0.1 mm to about 1.0 mm and an average pore diameter from about 50 nm to about 250 nm.

11. The process according to claim 8, wherein:
the oxoacid anion-substituted polyaromatic resin is formed into a bead, supported onto an inert inorganic support, supported onto an inert organic support, or used in the absence of a support; and
the oxoacid anion-substituted polyaromatic resin is arranged as a fixed bed, a bubbling bed, a moving bed, or a stirred bed.

12. The process according to claim 8, wherein:
the first ligand and the second ligand are selected independently from a diphosphine ligand, a diamine ligand, a diene ligand, a diether ligand, or dithioether ligand; and
the associated metal cations are selected from a Group 1, 2, 12, or 13 metal.

13. The process according to claim 8, wherein the contacting step and/or the applying step is/are conducted at a pressure from 5 psig (34 KPa) to 10,000 psig (68,948 KPa) and at a temperature from 0° C. to 250° C.

14. The process according to claim 8, wherein the olefin comprises ethylene, propylene, butene, pentene, hexene, heptane, octene, or styrene.

15. The process according to claim 8, wherein the α,β-unsaturated carboxylic acid or the salt thereof is acrylic acid, methacrylic acid, 2-ethylacrylic acid, cinnamic acid, or a salt thereof.

16. The process according to claim 8, wherein the olefin is ethylene, and the step of contacting a transition metal precursor compound with the olefin and carbon dioxide ($CO_2$) is conducted using a constant addition of the olefin and carbon dioxide in an ethylene:$CO_2$ molar ratio of from 3:1 to 1:3, to provide the reaction mixture.

17. The process according to claim 8, further comprising a step of regenerating the oxoacid anion-substituted polyaromatic resin and associated metal cations by contacting a by-product acid form of the oxoacid anion-substituted polyaromatic resin with a metal-containing base and/or a metal-containing salt.

18. The process according to claim 17, wherein the metal-containing base comprises a carbonate, a hydroxide, an alkoxide, an aryloxide, or a sulfate, and the metal of the metal-containing base or the metal-containing salt comprises a sodium salt or a potassium salt.

19. The process according to claim 17, further comprising a step of regenerating the oxoacid anion-substituted polyaromatic resin and associated metal cations by contacting a by-product resin that is generated from the process with an aqueous sodium ion (Na$^+$) source.

20. The process according to claim 17, wherein the oxoacid anion-substituted polyaromatic resin is a sulfur oxoacid anion-substituted polyaromatic resin or the phosphorus oxoacid anion-substituted polyaromatic resin, and further comprising a step of regenerating the sulfur oxoacid anion-substituted polyaromatic resin and associated metal cations or the phosphorus oxoacid anion-substituted polyaromatic resin and associated metal cations by contacting a by-product resin that is generated from the process with a composition comprising aqueous sodium ion (Na$^+$).

21. The process according to claim 17, further comprising a step of regenerating the oxoacid anion-substituted polyaromatic resin and associated metal cations by contacting a by-product resin that is generated from the process with an aqueous acid and an aqueous brine.

22. The process according to claim 17, further comprising a step of regenerating the oxoacid anion-substituted polyaromatic resin and associated metal cations by contacting a by-product resin that is generated from the process with aqueous solution of about 5 wt % to about 15 wt % sodium chloride.

23. The process according to claim 17, further comprising a step of washing the regenerated oxoacid anion-substituted polyaromatic resin and associated metal cations with a solvent or the diluent following the regenerating step.

24. The process according to claim 17, wherein the step of regenerating the oxoacid anion-substituted polyaromatic resin and associated metal cations is carried out in the absence of a non-nucleophilic base.

25. A catalyst system for forming an α,β-unsaturated carboxylic acid or a salt thereof, the catalyst system comprising:
a) a transition metal precursor comprising a Group 8-10 transition metal and at least one first ligand;
b) optionally, at least one second ligand;
c) an olefin;
d) carbon dioxide ($CO_2$);
e) a diluent; and
f) an oxoacid anion-substituted styrene-based polymer or copolymer comprising a sulfonated, a phosphonated, a sulfinated, a thiosulfonated, or a thiosulfinated styrene polymer or styrene-divinylarene copolymer, further comprising associated metal cations.

26. The catalyst system according to claim 1, wherein the oxoacid anion-substituted polyaromatic resin comprises a crosslinked polystyrene sulfonate resin.

27. The catalyst system according to claim 1, wherein the associated metal cations are an alkali metal, an alkaline earth metal, or a combination thereof.

28. The catalyst system according to claim 1, wherein the diluent comprises an ether diluent, a carbonyl-containing diluent, an aromatic hydrocarbon diluent, a halogenated aromatic hydrocarbon diluent, or an alcohol diluent.

29. The catalyst system according to claim 1, wherein the first ligand, the second ligand, or both the first ligand and the second ligand comprises at least one of a nitrogen, phosphorus, sulfur, or oxygen heteroatom.

30. The catalyst system according to claim 1, wherein the first ligand, the second ligand, or both the first ligand and the second ligand is a bidentate ligand.

31. The catalyst system according to claim 1, wherein the first ligand is 1,5-cyclooctadiene and the second ligand is a diphosphine ligand, a diamine ligand, or an asymmetric ligand having one nitrogen and one phosphorus donor atom.

32. The catalyst system according to claim 1, wherein the metal of the transition metal precursor compound is a Group 8 metal.

33. The catalyst system according to claim 1, wherein the metal of the transition metal precursor compound is a Group 9 metal.

34. The catalyst system according to claim 1, wherein the metal of the transition metal precursor compound is a Group 10 metal.

* * * * *